(12) United States Patent
Duffield et al.

(10) Patent No.: US 9,707,100 B2
(45) Date of Patent: Jul. 18, 2017

(54) INTERBODY FUSION DEVICE AND SYSTEM FOR IMPLANTATION

(71) Applicant: Institute for Musculoskeletal Science and Education, Ltd., Wayne, PA (US)

(72) Inventors: William Duffield, Collegeville, PA (US); Katherine Elizabeth Brown, Garnet Valley, PA (US); James A. Sack, Elverson, PA (US)

(73) Assignee: Institute for Musculoskeletal Science and Education, Ltd., Wayne, PA (US)

( * ) Notice: Subject to any disclaimer, the term of this patent is extended or adjusted under 35 U.S.C. 154(b) by 0 days.

(21) Appl. No.: 15/194,323

(22) Filed: Jun. 27, 2016

(65) Prior Publication Data
US 2016/0374831 A1    Dec. 29, 2016

Related U.S. Application Data

(60) Provisional application No. 62/184,638, filed on Jun. 25, 2015, provisional application No. 62/210,707, (Continued)

(51) Int. Cl.
*A61F 2/44* (2006.01)
*A61F 2/46* (2006.01)
*A61F 2/30* (2006.01)

(52) U.S. Cl.
CPC ............ *A61F 2/4611* (2013.01); *A61F 2/447* (2013.01); *A61F 2/4455* (2013.01);
(Continued)

(58) Field of Classification Search
CPC ...... A61F 2/4611; A61F 2/4455; A61F 2/447; A61F 2002/4475; A61F 2220/0008
(Continued)

(56) References Cited

U.S. PATENT DOCUMENTS 4,554,914 A    11/1985  Kapp et al.
4,599,086 A    7/1986   Doty
(Continued)

FOREIGN PATENT DOCUMENTS

WO    2012047289 A1    4/2012
WO    2012117312 A2    9/2012
(Continued)

OTHER PUBLICATIONS

International Search Report and Written Opinion for PCT application PCT/US2016/039642 mailed Aug. 25, 2016.
(Continued)

*Primary Examiner* — Pedro Philogene
*Assistant Examiner* — David C Comstock
(74) *Attorney, Agent, or Firm* — Plumsea Law Group, LLC

(57) ABSTRACT

Implant fixation systems, kits and methods for interbody fusions are described herein. Preferably, the implant has a cage containing two deployable blades and one or more strike plates that are able to deploy the blades. The blades are positioned inside the cage such that one blade faces upward and the other blade faces downward. Protrusions on the ends of the blades fit into correspondingly shaped tracks on the interior surface of the cage, allowing movement of the blades inside the cage. The implant also has two wedge-shaped strike plates that fit into attachment regions located on the blades, which allow the strike plates to slide. Impaction of the strike plate(s) causes them to push the blades superiorly or inferiorly. In the impaction position, a portion of the blades protrudes beyond the superior and the inferior surfaces of the cage and fixes the cage in the adjacent vertebral bodies.

28 Claims, 21 Drawing Sheets

Related U.S. Application Data filed on Aug. 27, 2015, provisional application No. 62/236,698, filed on Oct. 2, 2015.

(52) U.S. Cl.
CPC .............. *A61F 2002/30579* (2013.01); *A61F 2002/4475* (2013.01); *A61F 2220/0008* (2013.01)

(58) Field of Classification Search
USPC .... 606/246, 279, 86 A, 99; 623/17.11–17.16
See application file for complete search history.

(56) References Cited

U.S. PATENT DOCUMENTS

| | | | |
|---|---|---|---|
| 4,636,217 A | | 1/1987 | Ogilvie et al. |
| 4,892,545 A | * | 1/1990 | Day .................. A61F 2/44 606/246 |
| 5,443,467 A | | 8/1995 | Biedermann |
| 5,522,899 A | | 6/1996 | Michelson |
| 5,609,635 A | | 3/1997 | Michelson |
| 5,653,708 A | | 8/1997 | Howland |
| 5,667,508 A | | 9/1997 | Errico |
| 5,683,394 A | | 11/1997 | Rinner |
| 5,702,391 A | | 12/1997 | Lin |
| 5,776,199 A | | 7/1998 | Michelson |
| 5,800,547 A | | 9/1998 | Schaefer et al. |
| 5,989,254 A | | 11/1999 | Katz |
| 6,102,949 A | | 8/2000 | Biedermann et al. |
| 6,102,950 A | | 8/2000 | Vaccaro |
| 6,113,601 A | | 9/2000 | Tatar |
| 6,113,638 A | | 9/2000 | Williams et al. |
| 6,179,873 B1 | | 1/2001 | Zientek |
| 6,251,140 B1 | | 6/2001 | Marino |
| 6,302,914 B1 | | 10/2001 | Michelson |
| 6,371,987 B1 | | 4/2002 | Weiland et al. |
| 6,447,544 B1 | | 9/2002 | Michelson |
| 6,447,546 B1 | | 9/2002 | Bramlet et al. |
| 6,447,547 B1 | | 9/2002 | Michelson |
| 6,454,805 B1 | | 9/2002 | Baccelli et al. |
| 6,478,823 B1 | | 11/2002 | Michelson |
| 6,527,803 B1 | | 3/2003 | Crozet et al. |
| 6,565,565 B1 | | 5/2003 | Yuan |
| 6,645,207 B2 | | 11/2003 | Dixon |
| 6,652,526 B1 | | 11/2003 | Arafiles |
| 6,656,181 B2 | | 12/2003 | Dixon |
| 6,733,535 B2 | | 5/2004 | Michelson |
| 6,755,829 B1 | | 6/2004 | Bono |
| 6,767,367 B1 | | 7/2004 | Michelson |
| 6,770,096 B2 | | 8/2004 | Bolger et al. |
| 6,786,903 B2 | | 9/2004 | Lin |
| 6,800,092 B1 | | 10/2004 | Williams et al. |
| 6,896,677 B1 | | 5/2005 | Lin |
| 6,923,830 B2 | | 8/2005 | Michelson |
| 6,926,737 B2 | | 8/2005 | Jackson |
| 6,981,975 B2 | | 1/2006 | Michelson |
| 6,986,771 B2 | | 1/2006 | Paul |
| 6,989,011 B2 | | 1/2006 | Paul |
| 7,066,961 B2 | | 6/2006 | Michelson |
| 7,081,117 B2 | | 7/2006 | Bono |
| 7,112,206 B2 | | 9/2006 | Michelson |
| 7,125,426 B2 | | 10/2006 | Moumene |
| 7,141,051 B2 | | 11/2006 | Janowski |
| 7,214,243 B2 | | 5/2007 | Taylor |
| 7,217,293 B2 | | 5/2007 | Branch, Jr. |
| 7,223,289 B2 | | 5/2007 | Trieu et al. |
| 7,264,621 B2 | | 9/2007 | Coates |
| 7,318,839 B2 | | 1/2008 | Malberg et al. |
| 7,338,491 B2 | | 3/2008 | Baker |
| 7,361,195 B2 | | 4/2008 | Schwartz et al. |
| 7,465,317 B2 | | 12/2008 | Malberg et al. |
| 7,503,924 B2 | | 3/2009 | Lee |
| 7,503,933 B2 | | 3/2009 | Michelson |
| 7,559,942 B2 | | 7/2009 | Paul |
| 7,569,074 B2 | | 8/2009 | Eisermann |
| 7,594,931 B2 | | 9/2009 | Louis |
| 7,594,932 B2 | | 9/2009 | Aferzon et al. |
| 7,604,656 B2 | | 10/2009 | Shluzas |
| 7,608,095 B2 | | 10/2009 | Yuan |
| 7,655,046 B2 | | 2/2010 | Dryer |
| 7,678,137 B2 | | 3/2010 | Butler |
| 7,704,279 B2 | | 4/2010 | Moskowitz et al. |
| 7,727,279 B2 | | 6/2010 | Zipnick et al. |
| 7,727,280 B2 | | 6/2010 | McLuen |
| 7,731,749 B2 | | 6/2010 | Biedermann |
| 7,731,751 B2 | | 6/2010 | Butler et al. |
| 7,731,753 B2 | | 6/2010 | Reo et al. |
| 7,744,649 B2 | | 6/2010 | Moore |
| 7,749,274 B2 | | 7/2010 | Razian |
| 7,758,644 B2 | | 7/2010 | Trieu |
| 7,766,946 B2 | | 8/2010 | Bailly |
| 7,766,967 B2 | | 8/2010 | Francis |
| 7,771,475 B2 | | 8/2010 | Michelson |
| 7,776,067 B2 | | 8/2010 | Jackson |
| 7,780,703 B2 | | 8/2010 | Yuan |
| 7,789,914 B2 | | 9/2010 | Michelson |
| 7,811,310 B2 | | 10/2010 | Baker |
| 7,819,901 B2 | | 10/2010 | Yuan |
| 7,833,252 B2 | | 11/2010 | Justis |
| 7,842,073 B2 | | 11/2010 | Richelsoph |
| 7,846,188 B2 | | 12/2010 | Moskowitz et al. |
| 7,857,857 B2 | | 12/2010 | Kim |
| 7,867,257 B2 | | 1/2011 | Na |
| 7,879,099 B2 | | 2/2011 | Zipnick et al. |
| 7,883,542 B2 | | 2/2011 | Zipnick et al. |
| 7,909,856 B2 | | 3/2011 | Yuan |
| 7,909,872 B2 | | 3/2011 | Zipnick et al. |
| 7,942,903 B2 | | 5/2011 | Moskowitz et al. |
| 7,942,910 B2 | | 5/2011 | Doubler |
| 7,942,911 B2 | | 5/2011 | Doubler |
| 7,951,173 B2 | | 5/2011 | Hammill, Sr. |
| 7,951,174 B2 | | 5/2011 | Kwak |
| 7,951,180 B2 | | 5/2011 | Moskowitz et al. |
| 7,955,359 B2 | | 6/2011 | Matthis |
| 7,955,363 B2 | | 6/2011 | Richelsoph |
| 7,967,850 B2 | | 6/2011 | Jackson |
| 7,972,363 B2 | | 7/2011 | Moskowitz et al. |
| 7,972,365 B2 | | 7/2011 | Michelson |
| 7,998,211 B2 | | 8/2011 | Baccelli et al. |
| 8,012,186 B2 | | 9/2011 | Pham |
| 8,021,430 B2 | | 9/2011 | Michelson |
| 8,034,086 B2 | | 10/2011 | Iott |
| 8,038,702 B2 | | 10/2011 | Yuan |
| 8,048,124 B2 | | 11/2011 | Chin |
| 8,057,519 B2 | | 11/2011 | Justis |
| 8,062,340 B2 | | 11/2011 | Berrevoets |
| 8,062,374 B2 | | 11/2011 | Markworth et al. |
| 8,062,375 B2 | | 11/2011 | Glerum |
| 8,070,812 B2 | | 12/2011 | Keller |
| 8,070,819 B2 | | 12/2011 | Aferzon et al. |
| 8,075,590 B2 | | 12/2011 | Janowski |
| 8,075,599 B2 | | 12/2011 | Johnson |
| 8,075,603 B2 | | 12/2011 | Hammill, Sr. |
| 8,075,618 B2 | | 12/2011 | Trieu et al. |
| 8,080,062 B2 | | 12/2011 | Armstrong et al. |
| 8,083,796 B1 | | 12/2011 | Raiszadeh et al. |
| 8,100,972 B1 | | 1/2012 | Bruffey et al. |
| 8,105,358 B2 | | 1/2012 | Phan |
| 8,142,479 B2 | | 3/2012 | Hess |
| 8,142,508 B1 | | 3/2012 | Bruffey et al. |
| 8,147,556 B2 | | 4/2012 | Louis |
| 8,162,989 B2 | | 4/2012 | Khalili |
| 8,167,793 B2 | | 5/2012 | Scott |
| 8,167,950 B2 | | 5/2012 | Aferzon et al. |
| 8,187,332 B2 | | 5/2012 | McLuen |
| 8,192,495 B2 | | 6/2012 | Simpson et al. |
| 8,216,313 B2 | | 7/2012 | Moore |
| 8,221,502 B2 | | 7/2012 | Branch, Jr. |
| 8,231,676 B2 | | 7/2012 | Trudeau et al. |
| 8,241,294 B2 | | 8/2012 | Sommerich et al. |
| 8,241,341 B2 | | 8/2012 | Walker |
| 8,241,363 B2 | | 8/2012 | Sommerich et al. |
| 8,257,370 B2 | | 9/2012 | Moskowitz et al. |
| 8,257,439 B2 | | 9/2012 | Zeegers |

(56) References Cited

U.S. PATENT DOCUMENTS

| | | |
|---|---|---|
| 8,257,443 B2 | 9/2012 | Kamran et al. |
| 8,267,997 B2 | 9/2012 | Colleran |
| 8,273,125 B2 | 9/2012 | Baccelli et al. |
| 8,292,958 B1 | 10/2012 | Bruffey et al. |
| 8,328,870 B2 | 12/2012 | Patel et al. |
| 8,343,219 B2 | 1/2013 | Allain |
| 8,353,913 B2 | 1/2013 | Moskowitz et al. |
| 8,361,148 B2 | 1/2013 | Malberg et al. |
| 8,366,774 B1 | 2/2013 | Bruffey et al. |
| 8,377,133 B2 | 2/2013 | Yuan et al. |
| 8,377,138 B2 | 2/2013 | Reo et al. |
| 8,388,688 B2 | 3/2013 | Moore |
| 8,394,145 B2 | 3/2013 | Weiman |
| 8,409,285 B2 | 4/2013 | Keller |
| 8,425,528 B2 | 4/2013 | Berry et al. |
| 8,435,296 B2 | 5/2013 | Kadaba et al. |
| 8,435,301 B2 | 5/2013 | Gerber et al. |
| 8,444,696 B2 | 5/2013 | Michelson |
| 8,454,623 B2 | 6/2013 | Patel et al. |
| 8,460,388 B2 | 6/2013 | Kirwan |
| 8,512,407 B2 | 8/2013 | Butler et al. |
| 8,512,409 B1 | 8/2013 | Mertens et al. |
| 8,518,120 B2 | 8/2013 | Glerum |
| 8,523,909 B2 | 9/2013 | Hess |
| 8,523,946 B1 | 9/2013 | Swann |
| 8,540,769 B2 | 9/2013 | Janowski et al. |
| 8,545,562 B1 | 10/2013 | Materna et al. |
| 8,545,563 B2 | 10/2013 | Brun et al. |
| 8,556,979 B2 | 10/2013 | Glerum |
| 8,579,982 B2 | 11/2013 | Michelson |
| 8,597,353 B2 | 12/2013 | Kana et al. |
| 8,597,357 B2 | 12/2013 | Trudeau et al. |
| 8,597,360 B2 | 12/2013 | McLuen et al. |
| 8,617,245 B2 | 12/2013 | Brett |
| 8,679,183 B2 | 3/2014 | Glerum |
| 8,685,098 B2 | 4/2014 | Glerum |
| 8,685,104 B2 | 4/2014 | Lee et al. |
| 8,696,751 B2 | 4/2014 | Ashley et al. |
| 8,709,086 B2 | 4/2014 | Glerum |
| 8,715,350 B2 | 5/2014 | Janowski et al. |
| 8,734,516 B2 | 5/2014 | Moskowitz et al. |
| 8,747,444 B2 | 6/2014 | Moskowitz et al. |
| 8,753,394 B2 | 6/2014 | Zipnick I et al. |
| 8,795,335 B1 | 8/2014 | Abdou et al. |
| 8,795,367 B2 | 8/2014 | Zipnick |
| 8,795,368 B2 | 8/2014 | Trieu et al. |
| 8,814,879 B2 | 8/2014 | Trieu et al. |
| 8,828,018 B2 | 9/2014 | Ragab et al. |
| 8,845,738 B2 | 9/2014 | Michelson |
| 8,858,638 B2 | 10/2014 | Michelson |
| 8,864,829 B1 | 10/2014 | Bruffey et al. |
| 8,864,833 B2 | 10/2014 | Glerum |
| 8,888,853 B2 | 11/2014 | Glerum |
| 8,888,854 B2 | 11/2014 | Glerum |
| 8,894,710 B2 | 11/2014 | Simpson et al. |
| 8,900,310 B2 | 12/2014 | Carlson et al. |
| 8,906,101 B2 | 12/2014 | Lee et al. |
| 8,920,505 B2 | 12/2014 | Aferzon et al. |
| 8,932,355 B2 | 1/2015 | Grotz et al. |
| 8,932,359 B2 | 1/2015 | Brett |
| 8,940,048 B2 | 1/2015 | Butler et al. |
| 8,956,413 B2 | 2/2015 | Ashley et al. |
| 8,961,605 B2 | 2/2015 | Zipnick |
| 8,968,405 B2 | 3/2015 | Kirwan et al. |
| 8,979,933 B2 | 3/2015 | Vishnubholta et al. |
| 8,986,384 B2 | 3/2015 | Malberg et al. |
| 8,992,620 B2 | 3/2015 | Ashley et al. |
| 8,998,920 B2 | 4/2015 | Berry et al. |
| 9,005,293 B2 | 4/2015 | Moskowitz et al. |
| 9,034,041 B2 | 5/2015 | Wolters et al. |
| 9,039,770 B2 | 5/2015 | Aferzon et al. |
| 9,039,771 B2 | 5/2015 | Glerum |
| 9,107,760 B2 | 8/2015 | Walters |
| 9,107,761 B2 | 8/2015 | Lee et al. |
| 9,114,020 B2 | 8/2015 | Arginteanu |
| 9,119,732 B2 | 9/2015 | Schifano et al. |
| 9,155,553 B2 | 10/2015 | Zipnick |
| 9,168,152 B2 | 10/2015 | Raiszadeh et al. |
| 9,186,262 B2 | 11/2015 | McLuen et al. |
| 9,198,764 B2 | 12/2015 | Greenberg et al. |
| 9,198,771 B2 | 12/2015 | Ciupik |
| 9,198,774 B2 | 12/2015 | Pisharodi |
| 9,211,196 B2 | 12/2015 | Glerum |
| 9,220,606 B2 | 12/2015 | Janowski et al. |
| 9,226,836 B2 | 1/2016 | Glerum |
| 9,233,011 B2 | 1/2016 | Trudeau et al. |
| 9,248,028 B2 | 2/2016 | Gamache |
| 9,283,085 B2 | 3/2016 | Greenberg et al. |
| 9,283,087 B2 | 3/2016 | Lee et al. |
| 9,289,308 B2 | 3/2016 | Marino et al. |
| 9,301,854 B2 | 4/2016 | Moskowitz et al. |
| 9,351,847 B2 | 5/2016 | Reed et al. |
| 9,364,342 B2 | 6/2016 | Walkenhorst et al. |
| 9,370,435 B2 | 6/2016 | Walkenhorst et al. |
| 9,375,239 B2 | 6/2016 | Abdou |
| 2002/0120272 A1 | 8/2002 | Yuan |
| 2003/0004511 A1 | 1/2003 | Ferree |
| 2003/0109928 A1 | 6/2003 | Pasquet |
| 2003/0125742 A1 | 7/2003 | Yuan |
| 2003/0135279 A1 | 7/2003 | Michelson |
| 2003/0187433 A1 | 10/2003 | Lin |
| 2003/0187434 A1 | 10/2003 | Lin |
| 2004/0010312 A1 | 1/2004 | Enayati |
| 2004/0133280 A1 | 7/2004 | Trieu |
| 2004/0153068 A1 | 8/2004 | Janowski |
| 2004/0236330 A1 | 11/2004 | Purcell |
| 2004/0254644 A1 | 12/2004 | Taylor |
| 2005/0027362 A1 | 2/2005 | Williams et al. |
| 2005/0033296 A1 | 2/2005 | Bono |
| 2005/0033429 A1 | 2/2005 | Kuo |
| 2005/0049590 A1 | 3/2005 | Alleyne et al. |
| 2005/0060036 A1 | 3/2005 | Schultz et al. |
| 2005/0107788 A1 | 5/2005 | Beaurain |
| 2005/0131410 A1 | 6/2005 | Lin |
| 2005/0143825 A1 | 6/2005 | Enayati |
| 2005/0177154 A1 | 8/2005 | Moumene |
| 2005/0187548 A1 | 8/2005 | Butler |
| 2005/0197760 A1 | 9/2005 | Kaga |
| 2005/0228385 A1 | 10/2005 | Iott |
| 2005/0283157 A1 | 12/2005 | Coates |
| 2005/0288671 A1 | 12/2005 | Yuan |
| 2006/0004357 A1 | 1/2006 | Lee |
| 2006/0025767 A1 | 2/2006 | Khalili |
| 2006/0069436 A1 | 3/2006 | Sutton et al. |
| 2006/0095136 A1 | 5/2006 | McLuen |
| 2006/0122701 A1* | 6/2006 | Kiester .............. A61F 2/447 623/17.11 |
| 2006/0129149 A1 | 6/2006 | Iott |
| 2006/0149241 A1 | 7/2006 | Richelsoph |
| 2006/0161152 A1 | 7/2006 | Ensign |
| 2006/0217716 A1 | 9/2006 | Baker |
| 2006/0241764 A1 | 10/2006 | Michelson |
| 2006/0247636 A1 | 11/2006 | Yuan |
| 2006/0247776 A1 | 11/2006 | Kim |
| 2006/0264933 A1 | 11/2006 | Baker |
| 2006/0276789 A1 | 12/2006 | Jackson |
| 2006/0276899 A1 | 12/2006 | Zipnick et al. |
| 2006/0276901 A1 | 12/2006 | Zipnick et al. |
| 2006/0276902 A1 | 12/2006 | Zipnick et al. |
| 2006/0282074 A1 | 12/2006 | Renaud |
| 2006/0293665 A1 | 12/2006 | Shluzas |
| 2007/0050032 A1 | 3/2007 | Gittings et al. |
| 2007/0055235 A1 | 3/2007 | Janowski |
| 2007/0055241 A1 | 3/2007 | Matthis |
| 2007/0088357 A1 | 4/2007 | Johnson |
| 2007/0161999 A1 | 7/2007 | Biedermann |
| 2007/0162130 A1 | 7/2007 | Rashbaum |
| 2007/0213731 A1 | 9/2007 | Prusmack |
| 2007/0233078 A1 | 10/2007 | Justis |
| 2007/0233080 A1 | 10/2007 | Na |
| 2007/0270813 A1 | 11/2007 | Garamszegi |
| 2007/0270960 A1 | 11/2007 | Bonin et al. |
| 2007/0270961 A1 | 11/2007 | Ferguson |
| 2007/0282341 A1 | 12/2007 | Hes |

(56) References Cited

U.S. PATENT DOCUMENTS

| | | |
|---|---|---|
| 2008/0015580 A1 | 1/2008 | Chao |
| 2008/0015584 A1 | 1/2008 | Richelsoph |
| 2008/0015597 A1 | 1/2008 | Whipple |
| 2008/0021562 A1 | 1/2008 | Huppert |
| 2008/0027550 A1 | 1/2008 | Link et al. |
| 2008/0045953 A1 | 2/2008 | Garamszegi |
| 2008/0045955 A1 | 2/2008 | Berrevoets |
| 2008/0051901 A1 | 2/2008 | deVilliers |
| 2008/0051902 A1 | 2/2008 | Dwyer |
| 2008/0133017 A1 | 6/2008 | Beyar et al. |
| 2008/0147121 A1 | 6/2008 | Justis |
| 2008/0167716 A1 | 7/2008 | Schwartz et al. |
| 2008/0177322 A1 | 7/2008 | Davis |
| 2008/0177332 A1 | 7/2008 | Reiley |
| 2008/0183215 A1 | 7/2008 | Altarac |
| 2008/0195159 A1 | 8/2008 | Kloss |
| 2008/0200956 A1 | 8/2008 | Beckwith |
| 2008/0234686 A1 | 9/2008 | Beaurain |
| 2008/0287998 A1 | 11/2008 | Doubler |
| 2008/0294203 A1 | 11/2008 | Kovach |
| 2008/0312743 A1 | 12/2008 | Vila |
| 2009/0030457 A1 | 1/2009 | Janowski |
| 2009/0036929 A1 | 2/2009 | Reglos |
| 2009/0062866 A1 | 3/2009 | Jackson |
| 2009/0082819 A1 | 3/2009 | Blain |
| 2009/0164020 A1 | 6/2009 | Janowski et al. |
| 2009/0198241 A1 | 8/2009 | Phan |
| 2009/0198245 A1 | 8/2009 | Phan |
| 2009/0198338 A1 | 8/2009 | Phan |
| 2009/0270992 A1 | 10/2009 | Gerber et al. |
| 2009/0306720 A1 | 12/2009 | Doubler |
| 2009/0318974 A1 | 12/2009 | Yuan |
| 2010/0004694 A1 | 1/2010 | Little |
| 2010/0010547 A1 | 1/2010 | Beaurain |
| 2010/0016974 A1 | 1/2010 | Janowski |
| 2010/0063552 A1 | 3/2010 | Chin |
| 2010/0094352 A1 | 4/2010 | Iott |
| 2010/0114318 A1 | 5/2010 | Gittings et al. |
| 2010/0137920 A1 | 6/2010 | Hammill |
| 2010/0145455 A1 | 6/2010 | Simpson et al. |
| 2010/0161057 A1 | 6/2010 | Berry et al. |
| 2010/0185289 A1 | 7/2010 | Kirwan |
| 2010/0191246 A1 | 7/2010 | Howald et al. |
| 2010/0198273 A1 | 8/2010 | Kwak |
| 2010/0249933 A1 | 9/2010 | Trieu |
| 2010/0249935 A1 | 9/2010 | Slivka et al. |
| 2010/0268280 A1 | 10/2010 | Yuan |
| 2010/0280618 A1 | 11/2010 | Jodaitis |
| 2010/0305704 A1 | 12/2010 | Messerli et al. |
| 2010/0312279 A1 | 12/2010 | Gephart |
| 2011/0009911 A1 | 1/2011 | Hammill |
| 2011/0015742 A1 | 1/2011 | Hong |
| 2011/0035007 A1 | 2/2011 | Patel |
| 2011/0077739 A1 | 3/2011 | Rashbaum |
| 2011/0106166 A1 | 5/2011 | Keyer |
| 2011/0125196 A1 | 5/2011 | Quevedo |
| 2011/0137349 A1 | 6/2011 | Moskowitz et al. |
| 2011/0144701 A1 | 6/2011 | Altarac |
| 2011/0160779 A1 | 6/2011 | Schlaepfer |
| 2011/0166655 A1 | 7/2011 | Michelson |
| 2011/0196431 A1 | 8/2011 | Chao |
| 2011/0196494 A1 | 8/2011 | Yedlicka et al. |
| 2011/0202135 A1 | 8/2011 | Baek et al. |
| 2011/0208250 A1 | 8/2011 | Kwak |
| 2011/0208311 A1 | 8/2011 | Janowski |
| 2011/0208312 A1 | 8/2011 | Moskowitz et al. |
| 2011/0218579 A1 | 9/2011 | Jackson |
| 2011/0230971 A1 | 9/2011 | Donner |
| 2011/0270325 A1 | 11/2011 | Keyer |
| 2011/0307016 A1 | 12/2011 | Reglos |
| 2012/0010714 A1 | 1/2012 | Moskowitz et al. |
| 2012/0016477 A1 | 1/2012 | Metcalf et al. |
| 2012/0029569 A1 | 2/2012 | Iott |
| 2012/0029578 A1 | 2/2012 | Suh |
| 2012/0029644 A1 | 2/2012 | Markworth et al. |
| 2012/0035729 A1 | 2/2012 | Glerum |
| 2012/0053693 A1 | 3/2012 | Zeegers |
| 2012/0078371 A1 | 3/2012 | Gamache |
| 2012/0095559 A1 | 4/2012 | Woods et al. |
| 2012/0109318 A1 | 5/2012 | Gittings et al. |
| 2012/0116466 A1 | 5/2012 | Dinville |
| 2012/0143341 A1 | 6/2012 | Zipnick |
| 2012/0150300 A1 | 6/2012 | Nihalani |
| 2012/0150304 A1 | 6/2012 | Glerum |
| 2012/0150305 A1 | 6/2012 | Glerum |
| 2012/0158146 A1 | 6/2012 | Glerum |
| 2012/0158148 A1 | 6/2012 | Glerum |
| 2012/0191196 A1 | 7/2012 | Louis |
| 2012/0265248 A1 | 10/2012 | Delecrin |
| 2012/0265258 A1 | 10/2012 | Garvey |
| 2012/0277878 A1 | 11/2012 | Sommerich et al. |
| 2012/0296428 A1 | 11/2012 | Donner |
| 2012/0303064 A1 | 11/2012 | Walker |
| 2012/0330417 A1 | 12/2012 | Zipnick |
| 2012/0330419 A1 | 12/2012 | Moskowitz et al. |
| 2012/0330424 A1 | 12/2012 | Zeegers |
| 2012/0330425 A1 | 12/2012 | Zipnick |
| 2013/0013006 A1 | 1/2013 | Rashbaum |
| 2013/0018468 A1 | 1/2013 | Moskowitz et al. |
| 2013/0018469 A1 | 1/2013 | Moskowitz et al. |
| 2013/0023991 A1 | 1/2013 | Moskowitz et al. |
| 2013/0041408 A1 | 2/2013 | Dinville |
| 2013/0053962 A1 | 2/2013 | Moskowitz et al. |
| 2013/0110242 A1* | 5/2013 | Kirwan ................ A61F 2/4465 623/17.16 |
| 2013/0150968 A1 | 6/2013 | Dinville |
| 2013/0150969 A1 | 6/2013 | Zipnick |
| 2013/0166029 A1 | 6/2013 | Dinville |
| 2013/0274883 A1 | 10/2013 | McLuen et al. |
| 2013/0310935 A1 | 11/2013 | Swann |
| 2013/0338776 A1 | 12/2013 | Jones |
| 2014/0074241 A1 | 3/2014 | McConnell |
| 2014/0100663 A1 | 4/2014 | Messerli et al. |
| 2014/0114420 A1 | 4/2014 | Robinson |
| 2014/0121773 A1 | 5/2014 | Patel et al. |
| 2014/0148904 A1 | 5/2014 | Robinson |
| 2014/0148905 A1 | 5/2014 | Messerli et al. |
| 2014/0163682 A1 | 6/2014 | Lott et al. |
| 2014/0163683 A1 | 6/2014 | Seifert et al. |
| 2014/0172104 A1 | 6/2014 | Dugal et al. |
| 2014/0236297 A1 | 8/2014 | Iott |
| 2014/0249629 A1 | 9/2014 | Moskowitz et al. |
| 2014/0277509 A1 | 9/2014 | Robinson et al. |
| 2014/0277510 A1 | 9/2014 | Robinson et al. |
| 2014/0303731 A1 | 10/2014 | Glerum |
| 2014/0324171 A1 | 10/2014 | Glerum |
| 2014/0371795 A1 | 12/2014 | Hess et al. |
| 2014/0379085 A1 | 12/2014 | Duffield et al. |
| 2015/0012097 A1 | 1/2015 | Ibarra |
| 2015/0018952 A1 | 1/2015 | Ali |
| 2015/0025637 A1 | 1/2015 | Moskowitz et al. |
| 2015/0045893 A1 | 2/2015 | Dinville et al. |
| 2015/0100127 A1 | 4/2015 | Bal et al. |
| 2015/0105824 A1 | 4/2015 | Moskowitz et al. |
| 2015/0127107 A1 | 5/2015 | Kim et al. |
| 2015/0127109 A1 | 5/2015 | Brett et al. |
| 2015/0134064 A1 | 5/2015 | Grotz et al. |
| 2015/0142116 A1 | 5/2015 | Aferzon et al. |
| 2015/0209089 A1 | 7/2015 | Chataigner et al. |
| 2015/0250603 A9 | 9/2015 | Glerum |
| 2015/0250611 A1 | 9/2015 | Schifano et al. |
| 2015/0250612 A1 | 9/2015 | Schifano et al. |
| 2015/0265415 A1 | 9/2015 | Gittings et al. |
| 2015/0265416 A1 | 9/2015 | Aferzon et al. |
| 2015/0289988 A1 | 10/2015 | Ashley et al. |
| 2015/0305880 A1 | 10/2015 | Kim et al. |
| 2015/0305887 A1 | 10/2015 | McAtamney et al. |
| 2015/0320568 A1 | 11/2015 | Ameil et al. |
| 2015/0335372 A1 | 11/2015 | Schifano et al. |
| 2015/0342754 A1 | 12/2015 | Geebelen et al. |
| 2015/0374507 A1 | 12/2015 | Wolters et al. |
| 2016/0015526 A1 | 1/2016 | Ali |
| 2016/0030191 A1 | 2/2016 | McLuen et al. |
| 2016/0038299 A1 | 2/2016 | Chen et al. |

(56) References Cited

U.S. PATENT DOCUMENTS

| | | |
|---|---|---|
| 2016/0045326 A1 | 2/2016 | Hansen et al. |
| 2016/0045327 A1 | 2/2016 | Robinson et al. |
| 2016/0074172 A1 | 3/2016 | Lee et al. |
| 2016/0081813 A1 | 3/2016 | Greenberg et al. |
| 2016/0100953 A1 | 4/2016 | Dinville et al. |
| 2016/0106550 A1 | 4/2016 | Slivka et al. |
| 2016/0113777 A1 | 4/2016 | Gamache |
| 2016/0120657 A1 | 5/2016 | Trudeau et al. |
| 2016/0166395 A9 | 6/2016 | Weiman |
| 2016/0175107 A1 | 6/2016 | Janowski et al. |

FOREIGN PATENT DOCUMENTS

| | | |
|---|---|---|
| WO | 2013062716 | 5/2013 |
| WO | 2016010499 A1 | 1/2016 |

OTHER PUBLICATIONS

International Search Report and Written Opinion issued Aug. 25, 2016 for International Application No. PCT/US2016/039642.

\* cited by examiner

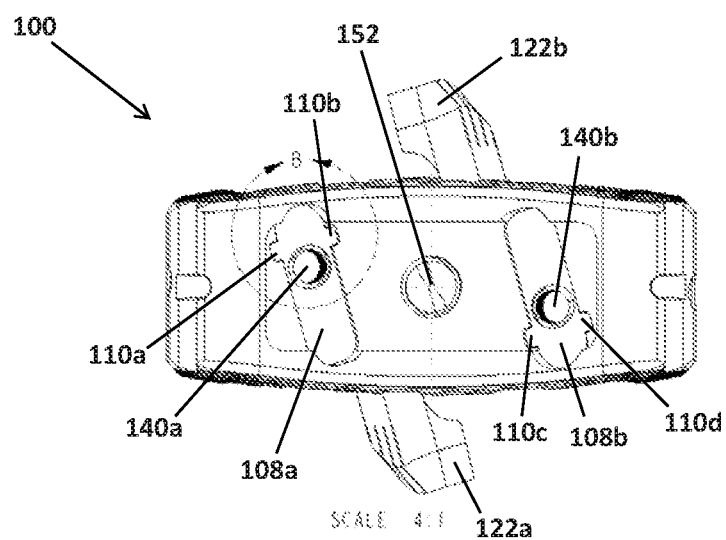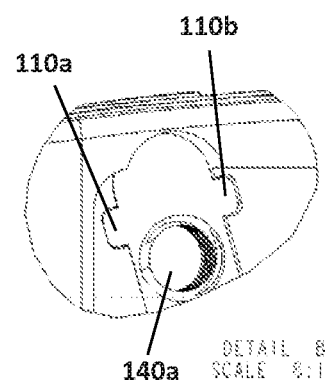
FIG. 7A
FIG. 7B

FIG. 11A
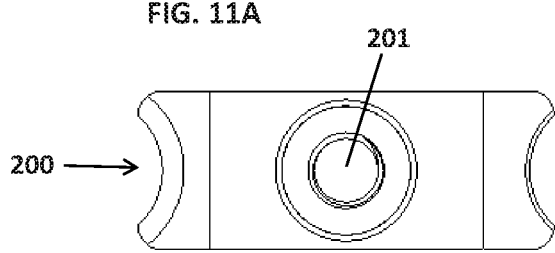
FIG. 11B
FIG. 11C
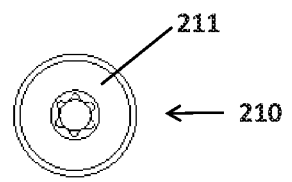
FIG. 11D
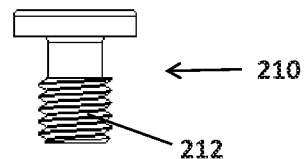

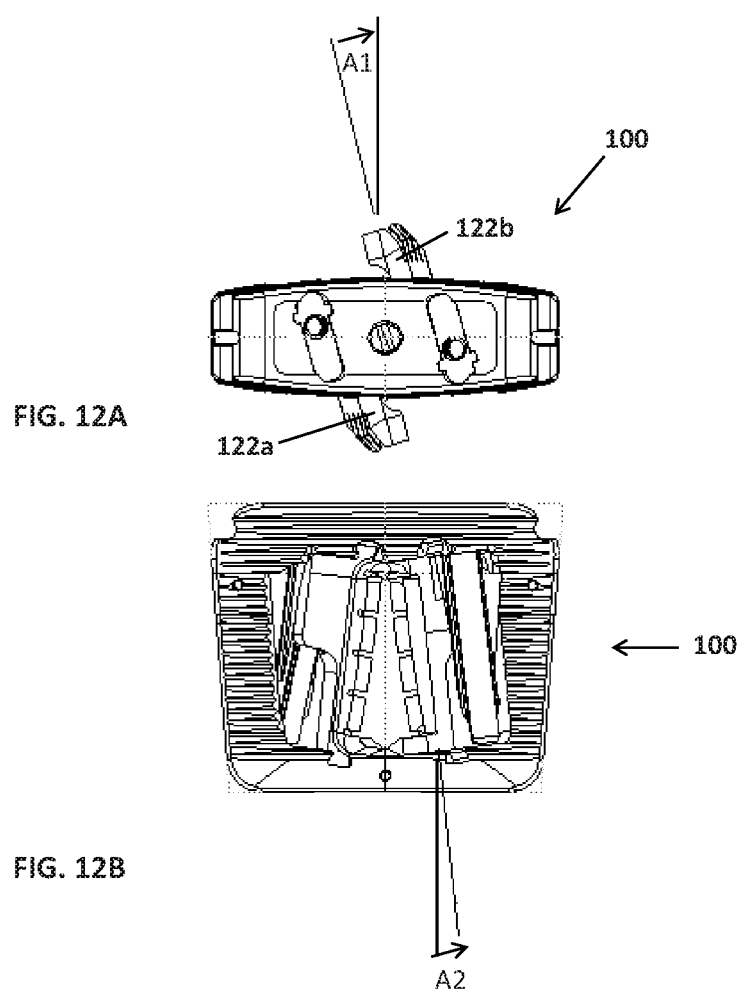

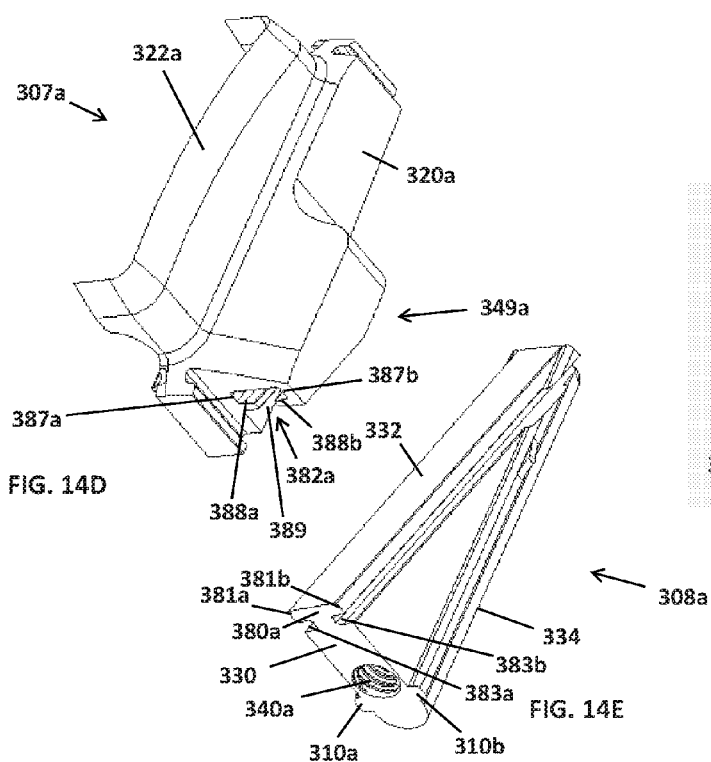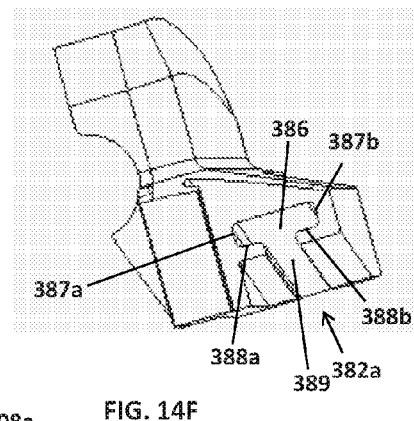

INTERBODY FUSION DEVICE AND SYSTEM FOR IMPLANTATION

CROSS-REFERENCE TO RELATED APPLICATIONS

The present application claims priority to U.S. application Ser. No. 62/184,638, filed on Jun. 25, 2015; U.S. Application No. 62/210,707, filed on Aug. 27, 2015; and U.S. Application No. 62/236,698, filed on Oct. 2, 2015, by William Duffield and Katherine Elizabeth Brown, the disclosures of which are incorporated herein by reference in their entirety.

FIELD OF THE INVENTION

The present invention relates generally to interbody fusion implants and methods, and systems for fixing such implants in place.

BACKGROUND OF THE INVENTION

Anterior lumbar interbody fusion (ALIF) is a type of spinal fusion that utilizes an anterior (front—through the abdominal region) approach to fuse the lumbar spine bones together. The intervertebral disc is removed and replaced with a bone (or metal) spacer. The anterior technique is often used when multiple spinal levels are being fused and multiple discs need to be removed. ALIF may be performed in conjunction with or without a posterior decompression (laminectomy) and/or instrumentation (use of metal screws/rods). The anterior approach is also used when only one spinal level is fused and a posterior decompression and/or instrumentation are not required. Although the anterior lumbar approach involves retracting (moving out of the way, temporarily) large blood vessels (e.g., aorta, vena cava) and the intestines, there is a wide exposure of the intervertebral disc without retraction of the spinal nerves and neurologic structures and therefore, a decreased risk of neurologic injury).

ALIF is commonly performed for a variety of painful spinal conditions, such as spondylolisthesis and degenerative disc disease.

The ALIF approach is advantageous in that, unlike the posterior lumbar interbody fusion (PLIF) and posterolateral gutter approaches, both the back muscles and nerves remain undisturbed.

Another advantage with the ALIF approach is that placing the bone graft in the front of the spine places it in compression, and bone in compression tends to fuse better.

Additionally, a much larger implant can be inserted through an anterior approach, and this provides for better initial stability of the fusion construct.

However, the ALIF procedure also involves resection of the anterior longitudinal ligament, which can destabilize the implant.

Therefore, surgeons often combine ALIF with a posterior approach (anterior/posterior fusions) because of the need to provide more rigid fixation than an anterior approach alone currently provides. Additionally, stabilization and fixation devices have been added to a standard interbody fusion spacer to stabilize and fix the spacer in place.

The lateral approach provides an alternate route to the spine that disturbs fewer structures and tissues. This, in combination with small incisions, means less discomfort for the patient and fewer risks of complications. With a lateral lumbar interbody fusion (lateral LIF), the surgeon approaches the back through a small incision in the side of the body, using special tools and techniques. A lateral LIF is also commonly referred to as DLIF® (Direct Lateral Interbody Fusion), XLIF® (eXtreme Lateral Interbody Fusion), and transpsoas interbody fusion.

Typically, patients who are candidates for this surgery are those who would have needed an incision in the abdomen in order for the surgeon to reach the area of concern. Approaching the spine through the abdomen means the surgeon must bypass large blood vessels, nerves, muscles, and organs that are in the way. This can prolong recovery following surgery and, in rare cases, cause complications such as nerve or blood vessel damage.

Many existing interbody fusion spacer systems require multiple actions on the part of the surgeon with respect to implant insertion, and fixation of the implant to the vertebral bodies.

For example, the INDEPENDENCE® Spacer System (Globus Medical, Inc.) integrates a stabilization plate and a PEEK interbody spacer into a preassembled system. INDEPENDENCE® also incorporates a smooth screw blocking mechanism, minimizing disruption to the anatomy surrounding the surgical site and may lessen the long term impact from surgery. However, this system requires multiple actions by a surgeon to insert and fix the system in place.

Additionally the use of a screw fixation system has a number of disadvantages. Screw fixation systems can require the use of awls, drills, and/or taps to prepare a hole in the vertebrae. Some screw systems require the use of screwdrivers having different lengths to insert the screw or an initial driver to insert the screw most of the way into the vertebrae and then a torque driver to execute the final tightening.

Screw fixation devices require a specific angle of insertion that requires a larger soft tissue exposure/corridor than necessary to insert the implant itself. Sometimes these angles require undue pressure on the surrounding soft tissues which could place abdominal viscera and blood vessels at risk. These fixed angles required to insert the screws can limit the ability to insert the fixation devices at the L5-S1 disc, where the symphysis pubis may inhibit access.

Additionally, the fixed angles for screw insertion and limited soft tissue exposure can place excess pressure on the insertion tool and cause the screw to be inserted inappropriately and possibly strip the screw at the bone-screw interface or the screw-anterior plate interface.

While overcoming some of the limitations associated with fixed-angle screw insertion some vertebral fixation systems utilize variable angle screw insertion, however these systems may not provide rigid fixation to the plate/implant and vertebrae.

Screw systems, fixed or variable angle, provide little surface area contact within the vertebra to adequately resist the forces of flexion, extension, rotation, and translation/shear. A fixation system that effectively neutralizes these forces is necessary for rigid fixation. Rigid fixation eliminates the need for supplemental external immobilization devices (braces) and allows early patient mobilization and return to more normal activity.

Instrumentation and specialized tools for insertion of an intervertebral implant is yet another design parameter to consider when designing a spacer. Spinal fusion procedures can present several challenges because of the small clearances around the spacer when it is being inserted into the desired position. For instance, the instrumentation used may securely grip the implant on opposing sides or surfaces. In U.S. Pat. No. 6,520,993 to James, et al., for example, the superior and inferior surfaces have one or more regions in which no gripping teeth are present. These protrusion-free zones enable the implant to be grasped and manipulated by elongate rectangular blades. However, the clearance required to insert the spacer must be higher than the spacer itself to accommodate the required instrumentation. For this reason, distraction of the treated area typically is greater than the size of the implant itself.

Similarly, with the gripping tools used to manipulate and insert the implant on the sides of the spacer, additional clearance typically is needed to accommodate the added width of the insertion tool blades. Such increases in height or width of the profile of the spacer, when in communication with instrumentation, require additional space in order to insert the spacer. In some circumstances, this requires increasing the size of the distracted area in the patient. Further, sometimes creating this additional space can be difficult.

There remains a need for improved fixation devices for use in interbody fusions, such as ALIF and lateral LIF.

Therefore it is an object of the invention to provide improved intervertebral implants and kits.

It is a further object of the invention to provide improved methods for achieving intervertebral fusions in the lumbar or cervical spine.

It is yet a further object of the invention to provide an implant that can be removed without destroying the implant.

SUMMARY OF THE INVENTION

Intervertebral implants, kits and methods for an anterior lumbar interbody fusion (ALIF) or a lateral lumbar interbody fusion (lateral LIF) are described herein. The intervertebral implant is a multi-component fusion device. The implant contains an implant body with a fixation system incorporated therein. The fixation system includes two deployable blades and one or more strike plates that are able to push the blades from a first insertion position to a second, impaction position.

The blades contain a blade region and a support region and are positioned inside the implant such that one blade is able to move superiorly and the other blade is able to move inferiorly when deployed. Typically, the support region has an outer surface, an inner surface and two ends, each of which contains a protrusion. Each protrusion fits in a unidirectional/axial track located on an interior surface of the implant body and allow for linear translation of the blade relative to the implant body. The protrusions on the ends of the support region of the blades fit inside and in sliding relation to the tracks, allowing the blades to slide in a general vertical motion or at a compound angle inside the implant. In some embodiments the protrusion is in the shape of a dovetail (referred to herein as "dovetail" or "dovetail protrusion"), and the tracks are correspondingly shaped dovetail tracks.

In a preferred embodiment, the implant also contains two strike plates that are in the shape of a right-angled wedge. The hypotenuse surface of each wedge fits into a track containing an angled ramp located on the support regions of the blades, allowing the strike plates to slide along the track from a first, insertion position to a second, impaction position. In some embodiments, the hypotenuse surface of each wedge is the upper surface of a protrusion (referred to herein as a "strike plate protrusion") that fits into and slides along a correspondingly shaped track in the support region of the blade. In certain embodiments track is in the shape of a T-shaped track that has an upper surface, two side surfaces, two lower surfaces, and a channel, configured to engage a correspondingly shaped and sized, T-shaped strike plate protrusion on the strike plate.

In the insertion position, the strike plates protrude from one side of the implant and the blades are contained inside the implant. Impaction of the strike plates into the implant causes them to slide along the ramps, pushing one blade superiorly and the other blade inferiorly along the tracks on the interior surfaces of the implant. In the resulting impaction position, the blade regions of the blades are pushed out of the implant, protrude past the superior and inferior surfaces of the implant and engage the superior and inferior vertebral bodies.

Following insertion of the implant into the spine and impaction of the blades, a front cover plate may be affixed to the surface of the implant through which the strike plates protrude when in the insertion position to prevent the strike plates from backing out.

If needed, the front cover plate can be removed and the blades can be retracted to allow for removal of the implant.

BRIEF DESCRIPTION OF THE DRAWINGS

FIGS. 1A, 1B, 1C, and 1D respectively show plan, perspective, elevation, and side views of the implant.

FIGS. 2A, 2B, 2C, and 2D respectively show plan, perspective, elevation, and side views of the implant.

FIG. 4B is a cross-sectional view of FIG. 4A taken at section F-F.

FIG. 5B is a cross-sectional view of FIG. 5A taken at section F-F.

FIGS. 7A and 7B show an elevation view (FIG. 7A) of the implant depicted in FIGS. 1A-1D in the impaction position with a magnified partial view (FIG. 7B) showing retention rails (110a-110d) on either side of the strike plates (108a and 108b).

FIG. 10A shows a perspective view of the implant in its final impaction position with a cover plate attached to the anterior side of the implant. FIG. 10B shows a perspective view of the implant in the insertion position.

FIGS. 11A and 11B show elevation and side views (respectively) of an exemplary cover plate that is attachable to the implant depicted in FIGS. 1A-1D. FIGS. 11C and 11D show elevation and side views (respectively) of an exemplary screw that can be used to secure the cover plate to the outer surface of the implant body after insertion.

FIGS. 12A and 12B show elevation and plan views of the implant depicted in FIGS. 1A-1D, with the angle of the blade labeled.

FIG. 13A shows a perspective view with the blade portion facing up. FIG. 13B shows a perspective view with the blade portion facing down and the angled ramp facing up. FIG. 13C shows another perspective view with the blade portion facing down and showing the interior surface of the blade. FIG. 13D shows another perspective view with the blade portion facing up and the support portion visible, which shows the outer surfaces of the blade. FIG. 13E shows a side view of a blade. FIG. 13F shows a cross sectional side view of a blade showing the angle between the ramp and plane (P). FIG. 13G shows a cross sectional perspective view of a blade showing the ramp on the support region of the blade.

FIG. 14A shows an elevation view with the strike plate in the impaction position. FIG. 14B shows a perspective view with the strike plate in the insertion position. FIG. 14C shows a side view, with the strike plate in the insertion position. FIGS. 14D and 14E show perspective views of a blade and a strike plate, respectively, where the support region of the blade has a T-shaped track to accommodate a T-shaped protrusion on the respective strike plate. FIG. 14F shows another perspective view of the blade depicted in FIG. 14D.

DETAILED DESCRIPTION OF THE INVENTION

I. Definitions

Figure 1A:
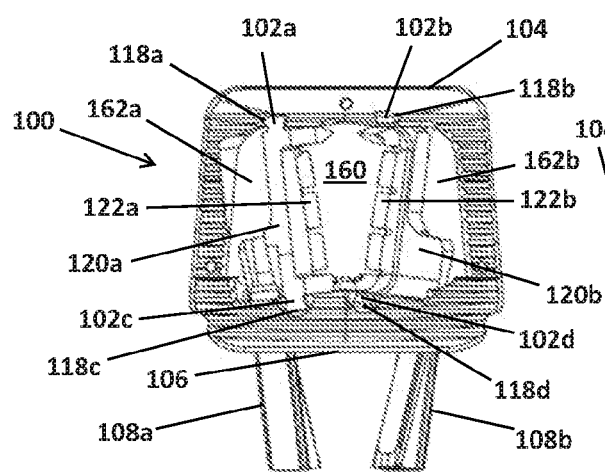
FIGS. 1A-1D show various views of an exemplary implant in its insertion position, with the strike plates protruding from the anterior side of the implant and the blades inside the implant.
Figure 1B:
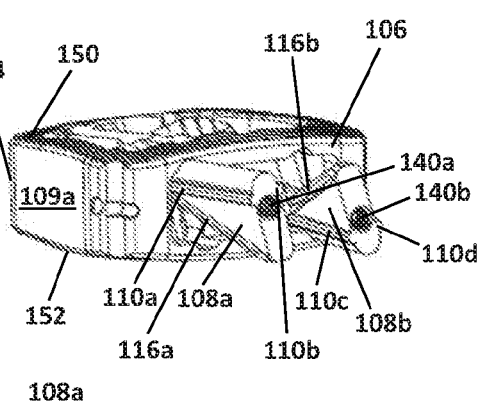
Figure 1C:
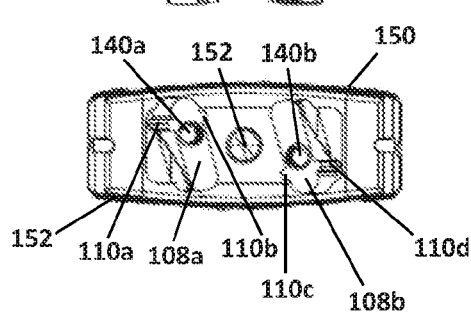
Figure 1D:
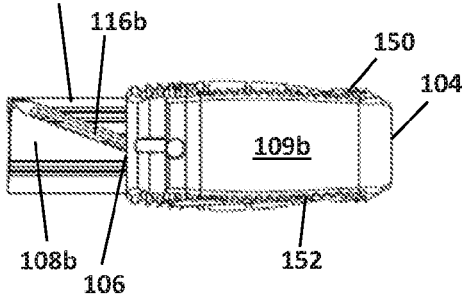
Figure 2A:
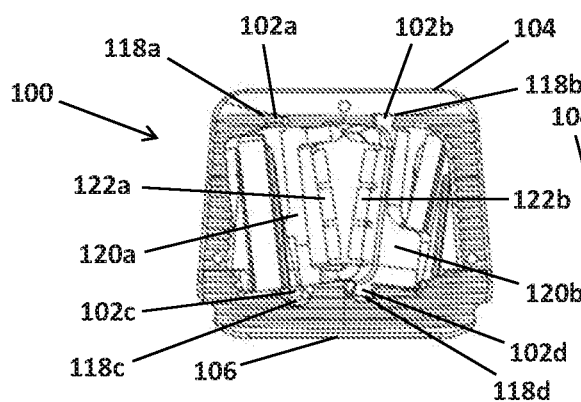
FIGS. 2A-2D show various views of the implant depicted in FIGS. 1A-1D in its impaction position. With the strike plates impacted, the two blades are forced superiorly and inferiorly, respectively.
Figure 2B:
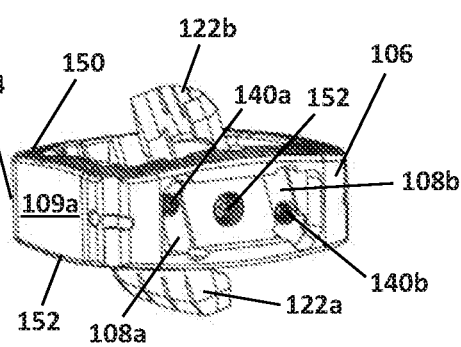
Figure 2C:
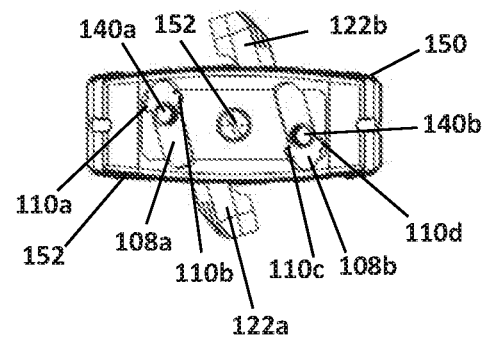
Figure 2D:
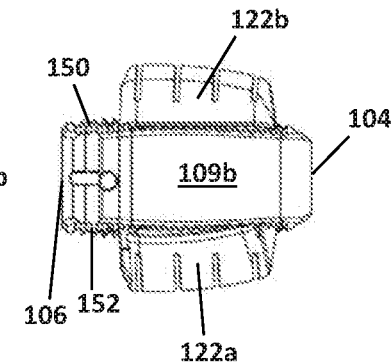

As used herein, the term "compound angle" refers to the resultant of two component angles where each component angle exists in a different plane. For example, component angle A1 and component angle A2 in FIGS. 12A and 12B lie in different planes. The resultant compound angle is defined by both of the component angles.

As used herein, the term "right-angled wedge" refers to a wedge that is shaped like a right-angled triangle when viewed from the side.

As used herein, the term "hypotenuse surface" refers to the outer surface of the longest side of a right-angled wedge in the strike plate, which is opposite the right angle.

As used herein, the term "impaction position" refers to the position in which the one or more strike plates are pushed into the implant, and the blade region of the blades protrudes past the superior and inferior surfaces of the implant.

As used herein, the term "insertion position" refers to the position in which the one or more strike plates protrude from one side of the implant body. In this position, the blades (i.e. both the support region and the blade region) are located and contained inside the implant.

As used herein, the term "retention bump" refers to a protrusion on a strike plate that keeps the blades in the insertion position until they are deployed.

II. Implant

A. Body

The intervertebral implants have a three dimensional body suitable for insertion between vertebrae.

The body is defined by two lateral side walls, an anterior side, a posterior side, a superior surface and an inferior surface. The body contains four interior surfaces (117a, 117b, etc.) corresponding with the lateral side walls, the anterior side and the posterior side, and six exterior surfaces (131a, 131b, etc.) corresponding with the lateral side walls, the anterior side, the posterior side, and the superior and inferior surfaces. The implant contains one or more openings, depending on the orientation of the blades and the number of strike plates, such as two or three openings, adjacent to and between the blades, which allow for the insertion of bone graft material. The implant allows the bone to grow through the implant and into the adjacent vertebral bodies. The openings define the void volume in the implant. The percent (%) void volume in each implant depends on the size, shape and type of implant. For example, the void volume in an implant, such as one used in an interbody fusion, can range from about 20% to about 60%. For ALIF implants, the % void volume ranges from 20% to 50%. Typically for lateral LIF implants the implants have a greater void volume compared to ALIF implants of a similar height. For example, for some lateral LIF implants, the % void volume ranges from 30% to 60%.

The implants and fixation systems may contain one or more threaded holes, slots or channels to mate with instruments to facilitate holding and inserting the implants. For example, the one or more strike plates may con am threaded connections or holes (140a, 140b, 340a, 340b) on their end(s) that connect to an insertion tool for insertion of the implant into or removal of the implant from the vertebral body.

The implant can be formed from any suitable biocompatible, non-degradable material with sufficient strength. Typical materials include titanium and inert, biocompatible polymers, such as polyether ether ketone (PEEK) (e.g. PEEK-OPTIMA®, Invibio Inc.). Optionally, the implant contains a radiopaque marker to facilitate visualization during imaging.

One embodiment of an exemplary implant (100) suitable for insertion into a patient using an anterior approach is illustrated FIGS. 1A-9B. As shown in FIG. 1A, the implant body is adapted for insertion within an intervertebral space between adjacent vertebral bodies and includes a first insertion side (posterior side) (104), a second side (anterior side) (106) opposite the first insertion side, a first lateral side portion (109a), a second lateral side portion (109b), a superior surface (150) and an inferior surface (152). In a preferred embodiment, the implant has a trapezoidal shape, with the posterior side being the shorter of the two parallel sides. One of ordinary skill in the art will appreciate that implants having other shapes may be used, with the particular shape of the implant selected for the particular insertion method and site.

The superior and inferior surfaces of the implant, which contact the superior vertebral body and the inferior vertebral body, respectively, typically contain teeth, knurling, ridges or similar projections, to aid in securing the implant to the vertebral endplate and preventing or reducing any shifting of the implant. This also provides initial stability of the implant between the two vertebral bodies following insertion into the intervertebral space.

The implants may be sized and configured for anterior, posterior or lateral approaches and insertion in the lumbar or cervical regions of the spine. In some embodiments the size of the implant body is 23 mm×28 mm. In some embodiments, the size of the implant body is 26 mm×32 mm. In other embodiments the size of the implant body is 32 mm×38 mm. The lordosis, or angle generated by tangent lines to the curved surfaces of adjacent vertebral endplates, can range from 0° to 30°, optionally from 0° to 10°, 5° to 10°, or 10° to 20°. For example, in some embodiments, the lordosis of the implant is 8°. In other embodiments, the lordosis is 15°. In some embodiments, the implant is 11 mm, 13 mm, 15 mm, 17 mm, 19 mm, or 21 mm tall when measured from the highest and lowest points on the superior and inferior surfaces respectively of either the implant body or the cover plate.

The particular surface shape and curvature, or taper in the anterior-posterior direction as well as between the lateral side surfaces depends upon the location at which the implant is intended to be inserted. For example, the anterior-to-posterior dimension (sagittal plane) of the Lateral LIF implant is less than the anterior-to-posterior dimension of the ALIF implant to allow insertion from a lateral approach. Typical anterior-to-posterior dimensions for a Lateral LIF implant range from about 18 to 26 mm, while for the ALIF, typical anterior-to-posterior dimensions range from about 23 to 32 mm. The left to right dimension of the lateral LIF implant is typically longer than the left to right dimension in an ALIF implant so that it can span the entire width of the vertebral body. The shape of the perimeter of the implant body can be modified for lumbar applications, or for other areas, such as in the cervical area of the spine. In some embodiments, the width (w) of the implant ranges from 28 mm to 38 mm. In a preferred embodiment, the width (w) is 28 mm. In some embodiments, the depth (d) of the implant ranges from 23 mm to 32 mm. In a preferred embodiment, the depth (d) is 23 mm. The height of ALIF and Lateral LIF implants generally ranges from 7 ram to 21 mm. In some preferred embodiments, the height (h) of the implant is 9 mm, 11 mm, 13 mm, or 15 mm. For the lateral LIF, the height typically ranges from 8 mm to 21 mm.

1. Tracks on an Interior Surface of the Implant Body

Figure 6A:
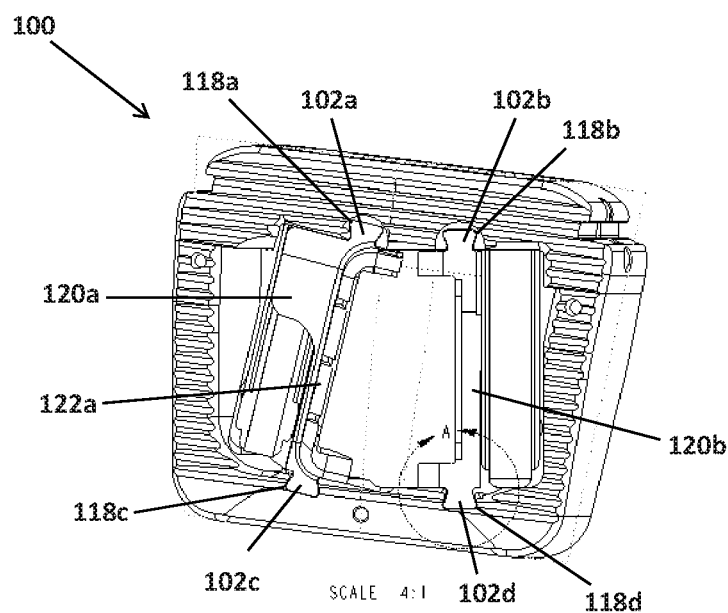
FIGS. 6A and 6B show a perspective view of the implant depicted in FIGS. 1A-1D (FIG. 6A) and a magnified partial view (FIG. 6B) showing a dovetail wedge (102b) protruding from the blade (107b).
Figure 6B:
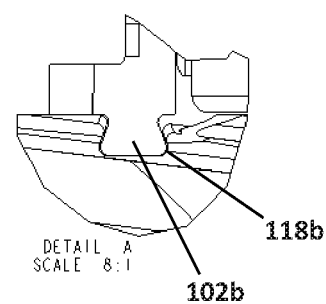
Figure 8A:
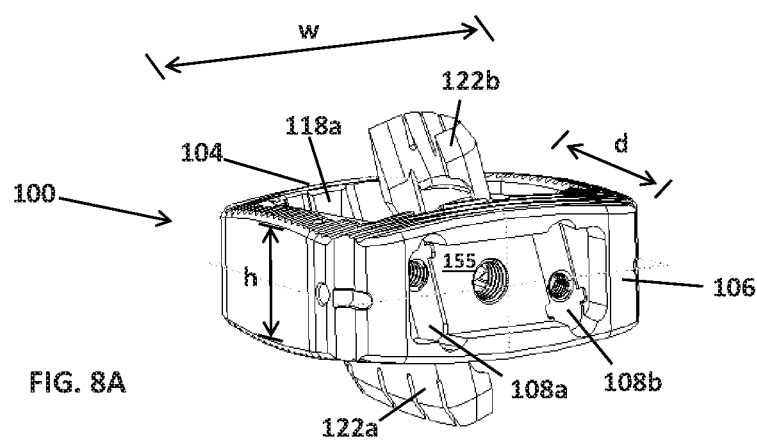
FIGS. 8A and 8B show perspective views of exemplary implants of different sizes.
Figure 8B:
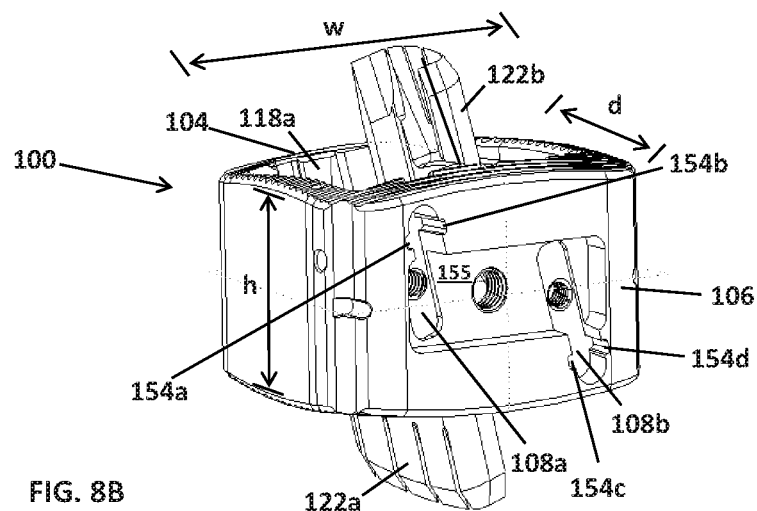

In a preferred embodiment, the implant contains four substantially vertical tracks on two of its interior surfaces, where the interior surfaces are opposite each other. For an ALIF, two of the tracks may be on the interior surface of the posterior side (118a, 118b), and two on the interior surface of the anterior side (118c, 118d). Preferably in the tracks have cross sections in the shape of dovetails (FIGS. 6A and 6B). The dovetail protrusions (102a-102d) located on both ends of the support regions of the two blades are located inside the dovetail tracks. The dovetail tracks allow the blades to slide inside the implant from the first insertion position to the second, impaction position.

One skilled in the art would understand that the track for sliding blades can adopt many different shapes as long as the tracks are complementary in shape to the protrusions on the ends of the support region for each blade. The cross-sectional shape may be a symmetric shape or a non-symmetric shape. Exemplary cross-sectional shapes include but are not limited to T-shapes, C-shapes, I-shapes, dovetailed shapes with angled sides, any portion of a circle, a triangle, an ellipse, a polygon, a star, a square, a rectangle, an oval, a hexagon, or an octagon.

In a preferred embodiment, the implant may contain one or more exterior surfaces, one or more depressions and or one or more screw holes that can be used to facilitate insertion of the implant and/or fixation of a cover plate to the exterior surface of the implant, such as to prevent the strike plates from moving after insertion of the implant between the vertebral bodies. For example, in a preferred embodiment useful for an ALIF, the implant may contain a screw hole (152) or other feature on the exterior surface (131b) of its anterior side (106), allowing the practitioner to attach an insertion tool to the insertion end of the implant and, optionally, to fix a cover plate over the anterior side after insertion of the implant between the vertebral bodies. In other embodiments, such as a LIF, the implant may contain on a lateral side or other side that is used for insertion a screw hole or other feature to facilitate insertion of the implant and, optionally to allow a practitioner to fix a cover plate over that side after insertion of the implant.

The implant can be implanted in the desired location in a patient using known surgical instruments. The number and position of access through-holes, e.g. two, three, four or the like, is dictated by the particular patient's anatomy or other surgical considerations, and is also not intended to be limited by the type of attachment mechanism between the implant and instrumentation.

The implant can be used for anterior, posterior or lateral approaches. The implants can be single-use devices. In some embodiments, the entire implant (including the fixation systems) can be removed from the patient and then later re-inserted.

B. Fixation Systems

The fixation systems described herein are integral with and can move from a first position (the "insertion position"), which allows the implant to maintain a low profile at the time of insertion, to a second position (the "impaction position"), in which the blades are deployed into the proximal superior and inferior vertebral bodies. In the deployed, impaction position, the blade region of the blades extends generally superiorly or inferiorly beyond the superior and inferior surfaces of the implant and into the adjacent superior and inferior vertebral bodies to prevent the implant from moving out of position over time. When the blades are deployed, the implant resists left to right rotation and resists flexion and/or extension. Additionally, the fixation elements are locked in place to prevent accidental removal from the implant. Following insertion in a disc space, the implant is contained within the excised disc space and does not protrude past the anterior wall of the vertebral body. Thus, the system has a zero anterior profile. Additionally, preparations of the anterior surface of the adjacent vertebral body/bodies are minimized because the implant does not lie against this surface.

The implant is pre-assembled with the fixation system. In the insertion position, as shown in FIGS. 1A-1D, 5A, 5B, and 10B, the strike plates extend beyond the anterior side and the blades (including the blade region) are completely inside the implant.

1. Blades

The implant contains one or more fixation elements to resist left to right rotation and to resist flexion and/or extension of the implant. Typically the fixation elements are blades.

The fixation system includes one or more blades (107a, 107b, 307a) as illustrated in FIGS. 3, 12A-12D, 13A-13E and 14A-14F. The blades include a blade region (122a, 122b, 322a, 322b) and a support region (120a, 120b, 320a, 320b).

a. Support Region

The support region has an outer surface (145a), an inner surface (146a) and two ends (148a, 148b), each of which have a protrusion that contacts a corresponding depression or track in an interior surface of the implant body. The protrusion functions as a joint to join two or more different elements in an implant together while allowing motion between the elements.

i. End Protrusions

As shown in the Figures, the protrusion at each end (148a, 148b) of the support region may be a dovetail protrusion (102a-102d) (also referred to herein as a "dovetail") that extends from the end of the support region and joins with an interior surface of a side wall of the body and allows the blade to move inferiorly or superiorly from a first, insertion position to second impaction position. The dovetail protrusion, as shown in the Figures typically has angled sides. Optionally the blade can move from an impaction position to the first (insertion position), to allow for removal of the implant, if needed. In the insertion position (shown in FIGS. 1A-1D, 5A, 5B, 10B), the blades, including the blade regions thereof, are located and contained inside the implant and are positioned such that the blade region of a first blade is directed superiorly and the blade region of the second blade is directed inferiorly.

The implant is inserted into the vertebral body in the insertion position. The blades are connected Co the implant via their protrusions, which fit into the tracks located on interior surfaces of the implant. The protrusions on the ends of the support region of the blades are in sliding relation Co the tracks, allowing the blades to slide anteriorly or superiorly inside the implant.

One skilled in the art would understand that the end protrusions can adopt many different shapes as long as the shape is complementary to the tracks on an interior surface of the implant. The cross-sectional shape may be a symmetric shape or a non-symmetric shape. Exemplary cross-sectional shapes include but are not limited to T-shapes, C-shapes, I-shapes, dovetailed shapes with angled sides, any portion of a circle, a triangle, an ellipse, a polygon, a star, a square, a rectangle, an oval, a hexagon, or an octagon. The corresponding tracks located on the interior surfaces of each implant have a shape that corresponds with the shape of the cross-section of the protrusion and maintains the protrusion in the track, while allowing it to slide along the track.

When sliding, the blades typically move generally vertically or at a compound angle, defined by a first angle in a first plane and a second angle in a second plane, relative to the body of the implant. For example, as shown in FIGS. 12A and 12B, angle A1 can range from 10° to 20° or any angle there between, such as 11°, 12°, 13°, 14°, 15°, 16°, 17°, 18°, 19°, or 20°. In a preferred embodiment, the A1 angle is 15°. Angle A2 can range from 5° to 15° or any angle there between, such as 5°, 6°, 7°, 8°, 9°, 10°, 11°, 12°, 13°, 14°, or 15°. In a preferred embodiment, the A2 angle is 7°. Optionally, the angle is not a compound angle and A2 is 0°. The blades are sufficiently strong such that they do not deform when moved from the insertion position to the impaction position.

b. Attachment Region(s)

The support region of the blades also contains one or more attachment regions (149a, 349a) configured to attach to one or more strike plates in a manner that keeps the strike plates and blades aligned as the strike plate moves in a longitudinal manner from a first position to a second position.

i. Attachment Region Track

The attachment region (149a, 349a) typically includes an attachment region track (114) defined by a ramp (115) and two side walls (124a, 124b). The opening between the side walls and the ramp defines a channel (189, 389).

The ramp (115) is configured to allow the hypotenuse surface (132) of the strike plate (108a, 108b) (sec FIGS. 9A, 9B, and 14B) to slide along its angled surface when the strike plate moves from a first, insertion position to a second, impaction position. The back portion of the ramp (115) may connect with a substantially horizontal surface (113) (see FIGS. 13F and 13G).

The blades are oriented in the implant body such that the angled ramps of the blades slope in opposite directions. For example, in an ALIF implant, the blades are positioned inside the implant body such that the tracks in the support region are proximal to the anterior side of the implant.

In some embodiments, the strike plates contain a protrusion on their hypotenuse surface that mates with a correspondingly shaped ramp in the support portion of the blade. For example, the ramp can be in the shape of a T-shaped track (382a), which is configured to engage a T-shaped protrusion (380a) of the hypotenuse surface (332) of the strike plate (308a) (see FIGS. 14A-F). In this embodiment, the T-shaped track contains an upper surface (386), two interior side wall surfaces (387a, 387b), two lower side wall protrusions (388a, 388b), and a channel defined by the upper surface, interior side wall surfaces and lower side wall protrusions (389) (see FIGS. 14D and 14F).

Figure 13A:
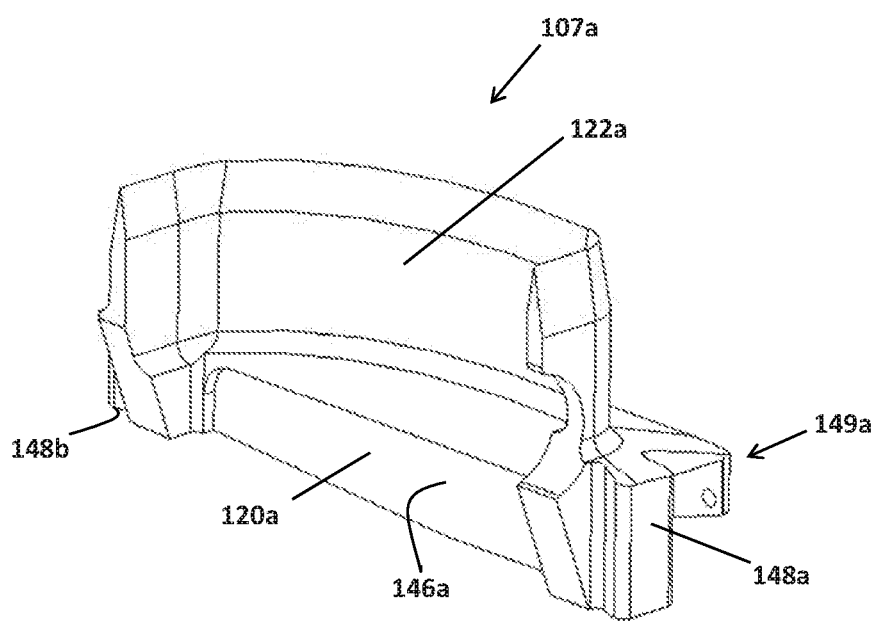
FIGS. 13A-13G show various views of an exemplary blade.
Figure 13B:
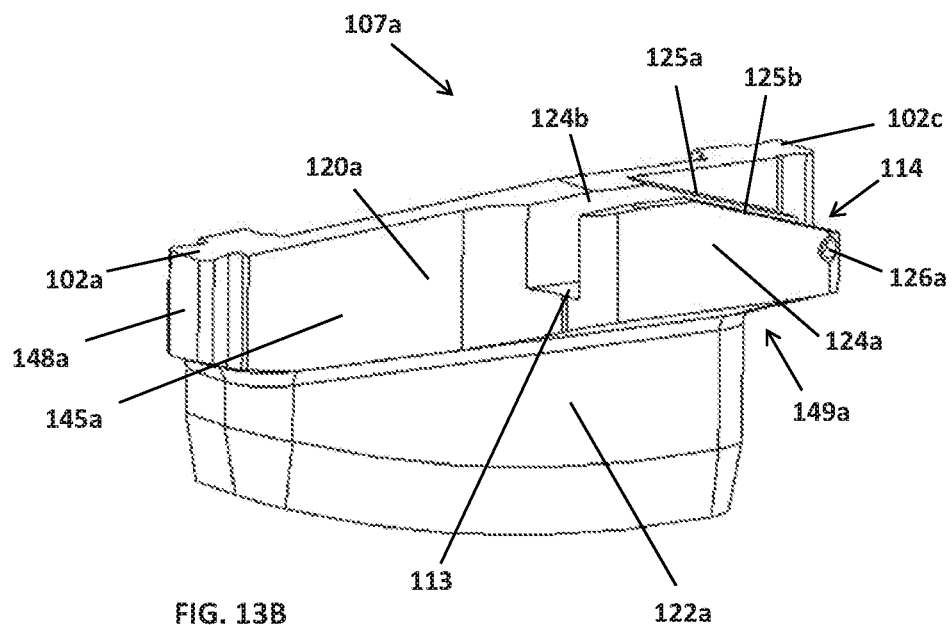
Figure 13C:
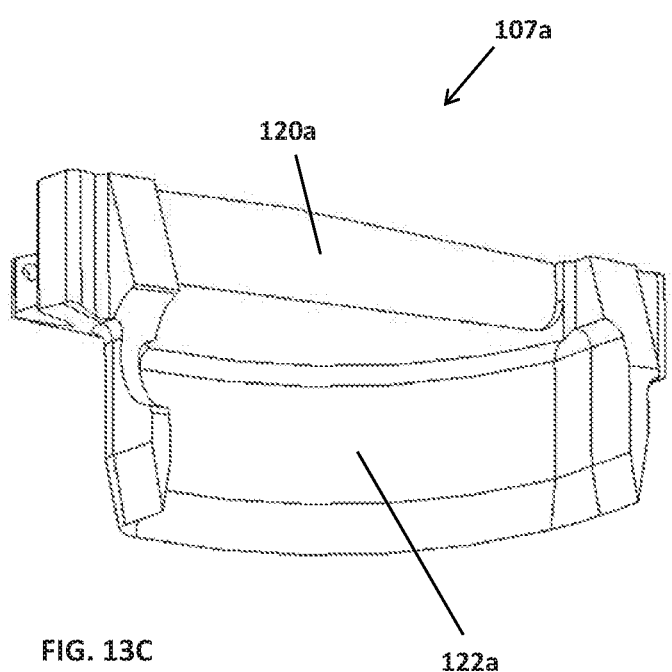
Figure 13D:
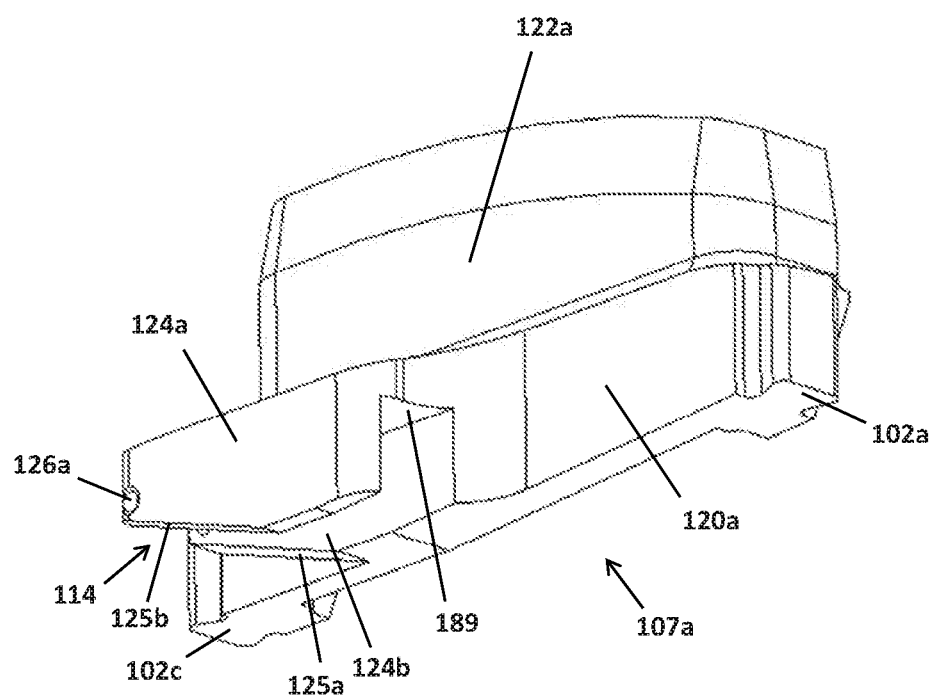
Figure 13E:
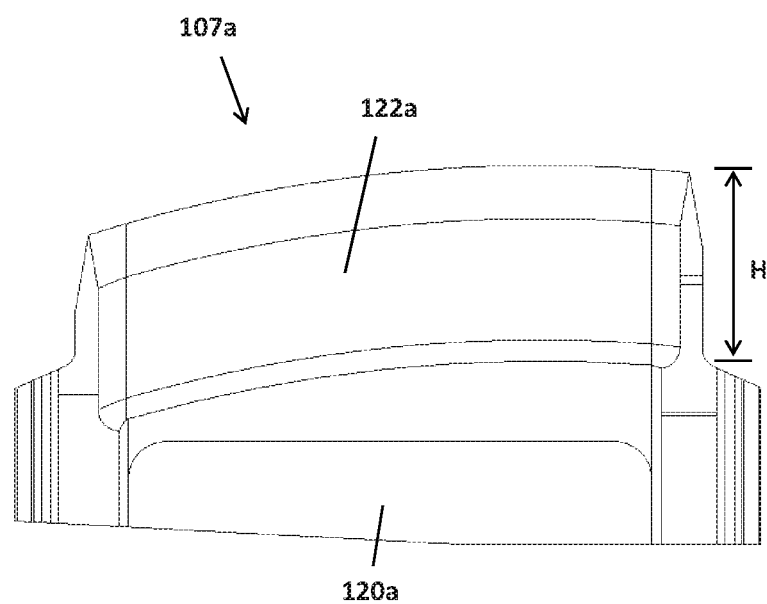
Figure 13F:
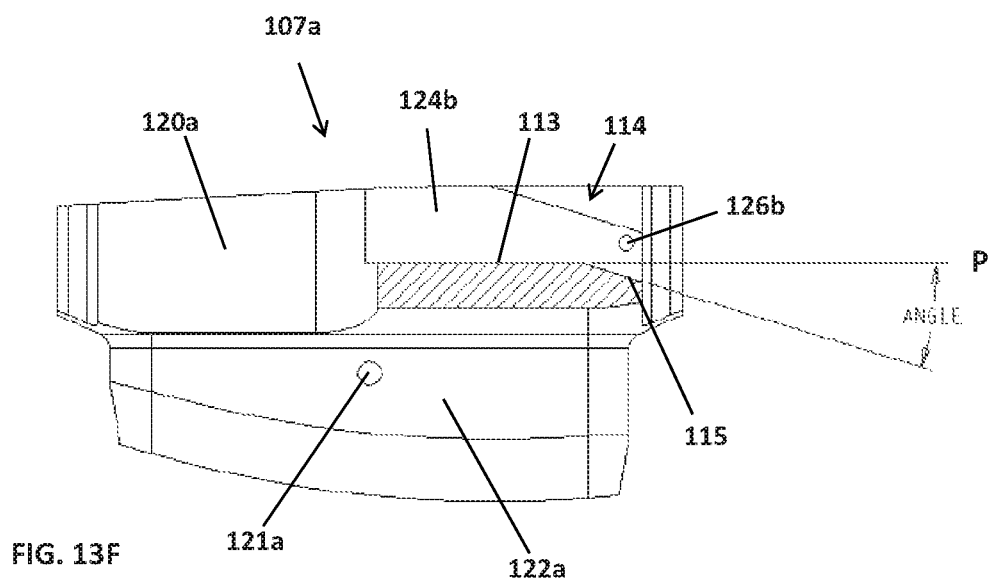
Figure 13G:
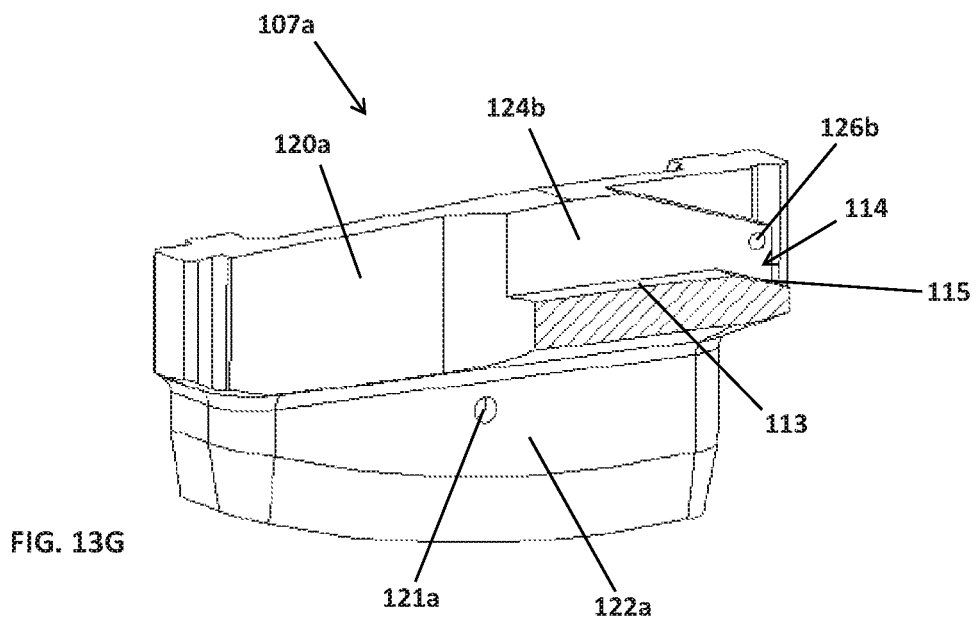
Figure 14A:
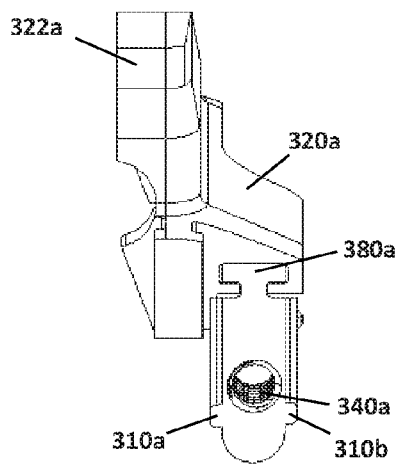
FIGS. 14A-14C show various views of a strike plate attached to a blade. In these Figures, the T-shaped protrusion of the strike plate fits into a correspondingly shaped T-shaped track in the support region of the blade.
Figure 14B:
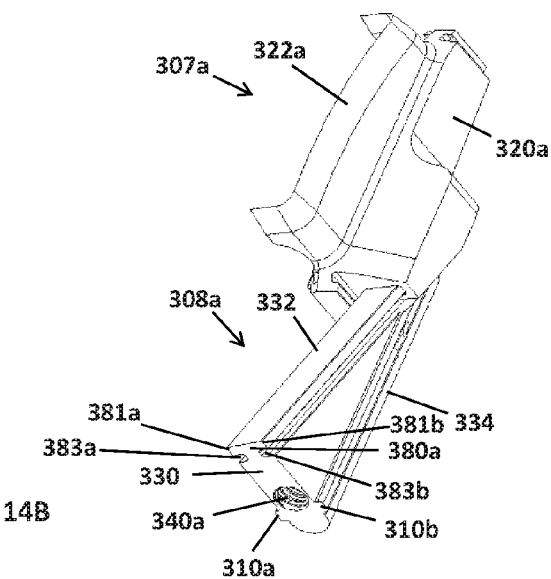
Figure 14C:
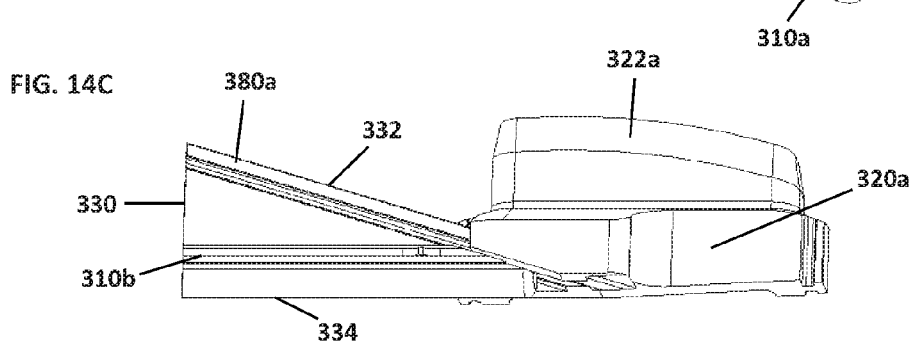

In some embodiments, the angle of the ramp (115) ranges from 20° to 35°, optionally from 21° to 33°, or any angle or range of angles there between, measured from the plane (P) (as identified on FIG. 13F). The angle for the ramp varies depending on the size of the implant. For example, for implants with a height (h) of 11 mm, preferably, the angle of the ramp is 21°. For implants with a height (h) of 13 mm, preferably, the angle of the ramp is 24°. For implants with a height (h) of 15 mm, preferably, the angle of the ramp is 26°.

Preferably the upper surface (125a) of the side wall (124a) slopes at the same angle as the angle of the ramp. This allows the strike plate to apply a force against the surface as it pushes the blade into the impaction position. Similarly, utilizing the same angle on the upper surface as in the ramp may facilitate removal of the blade, such as in a revision procedure or during initial placement of the implant in a patient. In these methods, the strike plates are pulled out of the impaction position and return to an insertion position, thereby removing the blades from the adjacent vertebral bodies.

c. Pin

Figure 4A:
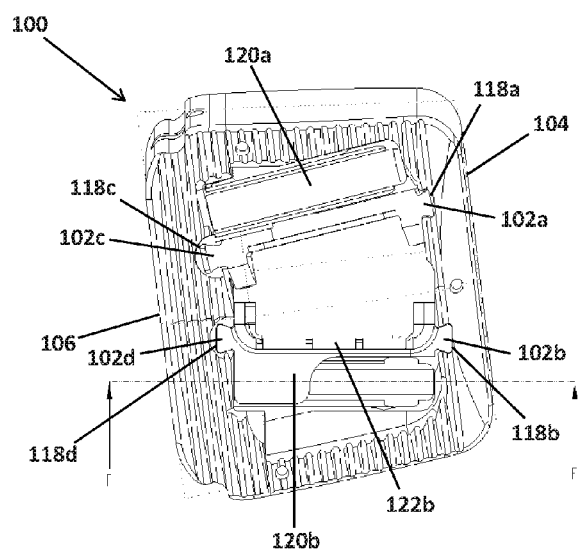
FIGS. 4A and 4B show perspective and cross-sectional perspective views respectively) of the implant depicted in FIGS. 1A-1D in the impaction position.
Figure 4B:
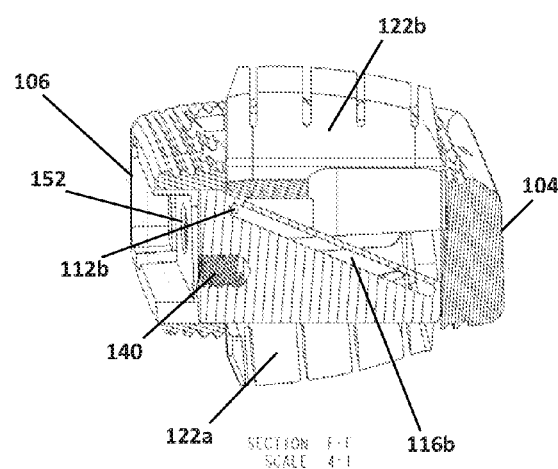
Figure 5A:
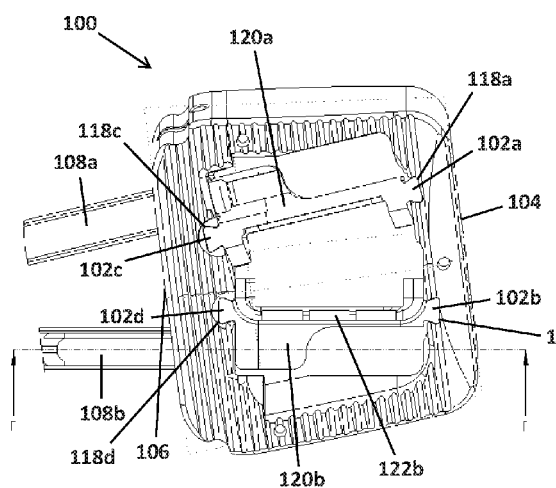
FIGS. 5A and 5B show perspective and cross-sectional perspective views, respectively, of the implant depicted in FIGS. 1A-1D in the insertion position, with the strike plates protruding from the anterior side of the implant.
Figure 5B:
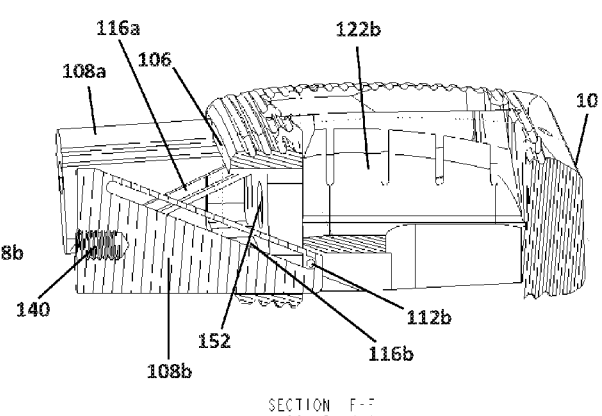

In some embodiments, the attachment region includes a pin to attach the strike plate and maintain it inside the track. For example, the attachment region may contain a cylindrical pin (112a or 112b), which is attached to the side walls, such as by fitting in circular depressions (126a, 126b). In these embodiments, the pin fits in and slides along an axial slot that runs generally parallel to the hypotenuse surface of the strike plate (see, e.g. the pin (112b) in the slot (116b) as depicted in FIGS. 4B and 5B).

Preferably, the side walls contain circular depressions (126a, 126b) proximal to the end of the ramp that is closest to the anterior side of the implant. In these embodiments, each of these depressions is configured to receive a pin (112a, 112b). In this embodiment, the strike plates can be attached to the support regions of the blades via a pin that slides through a slot in that runs parallel to the hypotenuse surface of a strike plate.

i. Track That Mates with Shape of the Strike Plate Protrusion

In other embodiments, the attachment region does not include a pin, rather the track has a shape that corresponds with and mates with the shape of a protrusion (which terminates on one side with the hypotenuse surface) on the strike plate (referred to herein as a "strike plate protrusion"). In these embodiments, the attachment region connects the support region of the blade to a strike plate via the axial track. For example, each of the side walls (124a, 124b) may contain a side wall protrusion (388a, 388b) that extends substantially perpendicular to the interior surface of the side wall (387a, 387b) and mates with a corresponding depression in the strike plate protrusion to retain the strike plate within the track.

For example, if the strike plate protrusion is in the shape of a dovetail, the channel of the track in the attachment region defines a similarly shaped dovetail cross-section, i.e. a dovetail track. Alternatively, if the strike plate protrusion is in the shape of a "T", such as depicted in FIGS. 14A-14F, the attachment region contains a channel with a similarly shaped T-shaped cross-section, i.e. a T-shaped track.

It is understood that alternative shapes for the channel in the track of the attachment region (and the corresponding protrusion on the strike plate) may be used as long as these shapes are complementary and allow the hypotenuse surface of the strike plate to slide along the track while remaining inside the track. The cross-sectional shape of the channel may be a symmetric shape or a non-symmetric shape. Exemplary cross-sectional shapes include but are not limited to T-shapes, C-shapes, I-shapes, dovetailed shapes with angled sides, any portion of a circle, a triangle, an ellipse, a polygon, a star, a square, a rectangle, an oval, a hexagon, or an octagon.

d. Blade Region

The blade region of an exemplary blade is shown in FIGS. 13A-13G. The height of the blade region is designated with H. In some embodiments, the height (H) of the blade region ranges from 3 mm to 9 mm. Preferably, the height of the blade region (H) is 5.75 mm. In other embodiments, such as the lateral LIP embodiment(s), the blade height can range from 3 mm to 18 mm.

When the implant is in the impaction positions, the length of engagement of the blade region in the adjacent vertebral body typically ranges from about 2.5 mm to 8.5 mm.

When the implant is in the impaction position and the blades are deployed, typically the total height of the implant from the tip of one blade to the tip of the other blade (including the deployed blades) increases by about 100 to 250% compared to the height of the implant in the insertion position.

As depicted in the Figures, in some embodiments the blade region (122a, 122b, 322a, 322b) of the blade has multiple projections that are separated by spaces. In other embodiments the blade region of the blade can also be a continuous surface.

Optionally, the blade region also has a marker that is visible by s suitable diagnostic method, such as x-ray. Suitable markers include a hole (121a) in any shape (e.g. circle or other shapes) or a marker formed from a material that is different than the material on the blade, which allows the practitioner to see when the blade is fully deployed when viewed on an X-Ray (see FIGS. 13F and 13G).

2. Strike Plates

Figure 3:
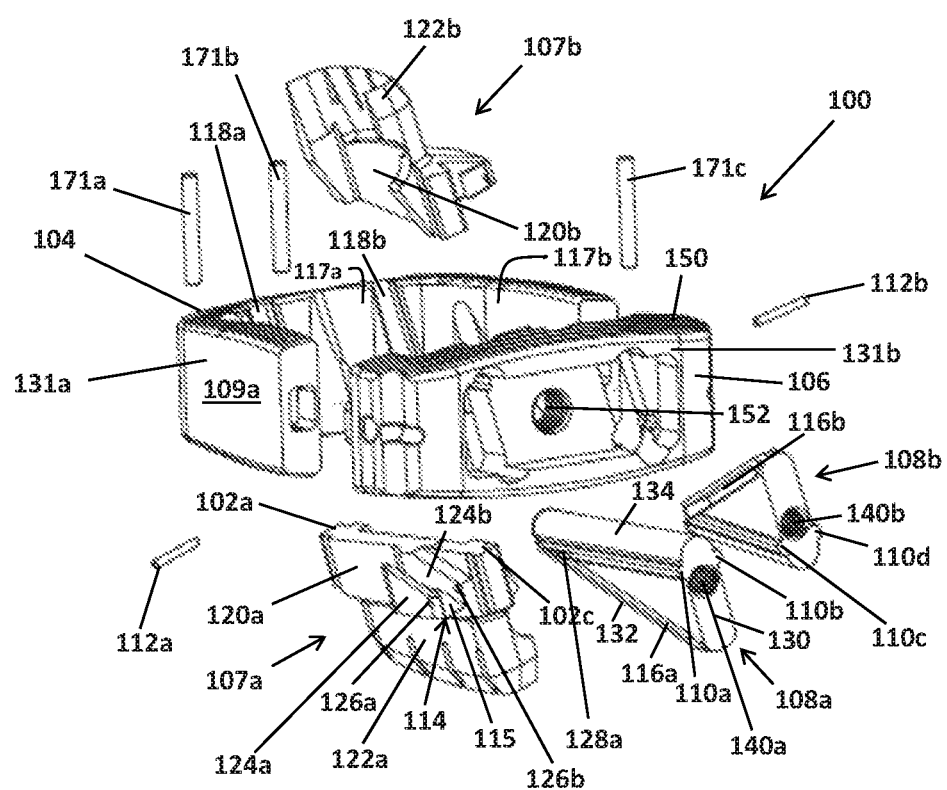
FIG. 3 shows an exploded view of the implant depicted in FIGS. 1A-1D.

In one embodiment, the strike plates (108a, 108b, 308a, 308b) are shaped like a right-angled wedge, formed of two surfaces (130, 134, 330, 334) adjacent to the right angle, and a hypotenuse surface (132, 332) opposite the right angle (as shown in FIGS. 9A, 9B, 14B, 14C, and 14E). The hypotenuse surface of each of the right-angled wedges fits into an angled ramp (114) that is located on the support region of the blade, in sliding relation thereto. The hypotenuse surface of the strike plate slides along the angled bottom surface of the ramp (FIG. 3).

In the insertion position, the strike plates (108a, 108b, 308a, 308b) protrude from one side of the exterior surface (131) of the implant. For example, for an ALIF implant, the strike plates protrude from the anterior side (106) of the implant (as seen in FIGS. 1A-1D, 5A, and 5B). For a LIF, the strike plates protrude from a lateral side of the implant. The strike plates are arranged in the implant such that the hypotenuse surfaces of the strike plates slope in opposite directions. The right angle of one strike plate is adjacent to the superior surface of the implant, and the right angle of the other strike plate is adjacent to the inferior surface of the implant. In this position the blades are contained inside the implant. The blades are positioned inside the implant such that when the strike plates are pushed into the implant, the hypotenuse surfaces of the strike plates slide along the ramps and push the blades inferiorly or superiorly inside the implant. In the resulting impaction position, at least some of each blade region is superior or inferior to the superior or inferior surface of the implant (as shown in FIGS. 2B-2D, 4B, 7A, 8A, 8B, and 10A).

Optionally, each strike plate also has bilateral retention rails (110a-110d, 310a, 310b), with one retention rail on each side of each strike plate. Each of the bilateral retention rails aligns with and fits inside a corresponding depression (154a-154d) on the anterior side (155) of the implant see, e.g. FIG. 8B). These rails secure the strike plates to the implant when they are fully extended beyond the anterior side (106) of the implant, such as when they are in the insertion position.

Additionally, each strike plate may contain an insertion region, such as an indent, depression, or a threaded hole (140a, 140b, 340a, 340b) to mate with a portion of an insertion device, to facilitate movement of the strike plates from the insertion position to the impaction position.

Figure 9A:
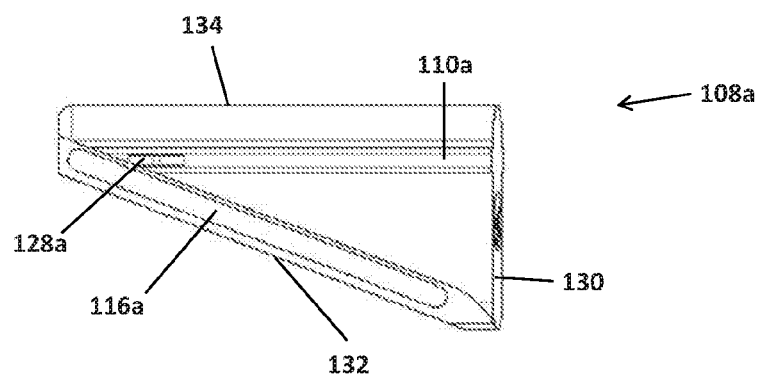
FIGS. 9A and 9B show a side view and perspective view, respectively, of an exemplary strike plate used in the implant depicted in FIGS. 1A-1D.
Figure 9B:
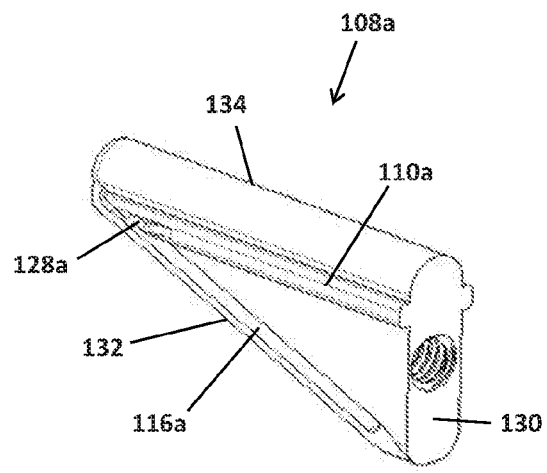
Figure 10A:
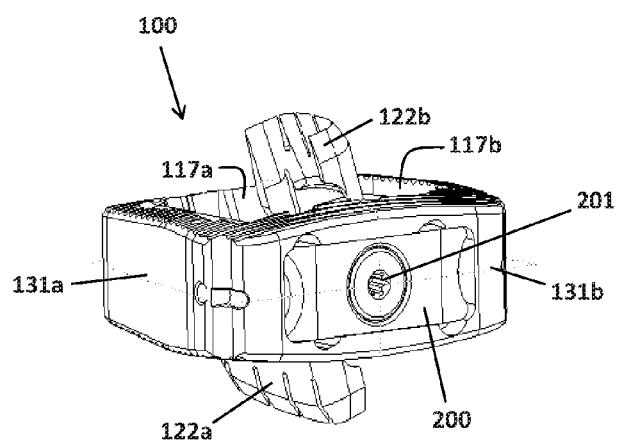
FIGS. 10A and 10B show perspective views of the implant depicted in FIGS. 1A-1D in the impaction and insertion positions.
Figure 10B:
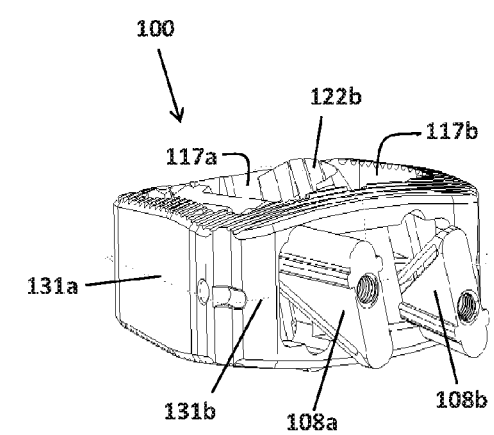

While the implant is loaded into an insertion device, the strike plates are prevented from being pushed into the implant by retention bumps (128a, 128b) present on the outer retention rail of each strike plate (FIGS. 9A and 9B). A retention bump is preferably located at the posterior end of each strike plate. Typically each strike plate contains one retention bump on one side, typically the outward facing retention rail (110a and 110d; 310a and 310b), at the posterior end. In the insertion position, the retention humps extend just beyond and are adjacent to a depression (154a and 154d) on the anterior side (155) of the implant. This prevents accidental deployment of the blades and damage of interior structures in the patient.

The retention bumps are small and protrude from the retention rail. In some embodiments this protrusion ranges from 0.1 mm to 0.4 mm, preferably 0.1 to 0.3 mm, and more preferably 0.24 mm. The resistance of the retention bumps against the anterior side can be overcome and the strike plates can be pushed into the implant and along the adjacent depression by applying a small force.

a. Slot

In one embodiment, each strike plate also contains an open slot (116a, 116b) that runs parallel to the hypotenuse surface of the wedge. Each strike plate is secured to a blade by a pin (112a, 112b) that fits through a first hole or depression (126a) in the first side wall (124a) of the angled ramp of the blade, through the open slot (116a, 116b) of the strike plate, and through a second hole or depression (126b) of the second angled side wall (124b) of the angled ramp of the blade.

b. Strike Plate Protrusion

In some embodiments, the hypotenuse surface of each strike plate is part of a protrusion (referred to herein as a "strike plate protrusion") that fits inside a correspondingly shaped attachment region track in the support region of the blade. For example, the strike plate protrusion can be in the shape of a T-shaped protrusion (380a) that fits into a T-shaped attachment region track (382a) (see FIGS. 14A-14F). In this embodiment the T-shaped protrusion has an upper hypotenuse surface (332), two outer lateral surfaces (381a, 381b), and a depression (383a, 383b) beneath each of the lateral surfaces, which defines a protrusion having a cross-section in the shape of a "T" (see FIGS. 14B and 14E).

One skilled in the art would understand that the strike plate protrusion can adopt many different shapes as long as the cross-section of the protrusion is complementary in shape to the cross section of the attachment region track. The strike plate protrusion of the track may be a symmetric shape or a non-symmetric shape. Exemplary cross-sectional shapes include hut are not limited to T-shapes, C-shapes, I-shapes, dovetailed shapes with angled sides, any portion of a circle, a triangle, an ellipse, a polygon, a star, a square, a rectangle, an oval, a hexagon, or an octagon.

3. Additional Components a. Cover Plate

Following insertion of the implant into the spine and impaction of the blades, a front cover plate (200) (FIGS. 11A and 11B) is typically added to prevent the one or more strike plates from backing out. The cover plate contains a central hole (201), which aligns with the screw hole (152) on a side (e.g., for an ALIF, the anterior side and for a lateral LIF, a lateral side) of the implant. A screw (210) is threaded through the central hole (201) and the screw hole (152) to secure the cover plate to the implant.

In a preferred embodiment, the process is reversible, allowing one to remove the implant, by first removing the cover plate. With the cover plate removed, each of the strike plates is accessible and can be engaged at the threaded connection (140, see FIGS. 4B and 5B) and attached to an insertion tool. The insertion tool can pull the strike plates back to the original insertion position, which pulls the blades out of the adjacent superior and inferior vertebral bodies. In this position, which corresponds with the insertion position, the blades, including the blade region, are inside the implant. This allows for the removal of the implant without destroying the implant, if necessary, such as in a revision procedure.

b. Insertion Tool

An implant insertion tool is used to insert the implant described herein into the desired location in the spine. The implant insertion tool contains threaded screws and/or gripping arms to connect with the insertion side of the implant. Additionally, typically the insertion tool contains threaded screws positioned and sized to fit in the corresponding threaded connections (140) in the strike plates to push the strike plates into the impaction position. However, alternative elements may be present on the insertion tool to connect it with the implant.

III. Kit

The implant may be provided as part of a kit for an ALIF or a LIF. The kit may contain at least one intervertebral implant as described above, and a cover plate. The kit may also contain an insertion tool. The kit also typically contains instructions for care and insertion of the spinal fixation system. In some embodiments, more than one implant is provided in the kit. Preferably, the kit contains a plurality of different sized implants to allow for use with patients with different anatomies.

It may not be clear what size implant is needed until the surgery has begun. Having a kit that provides several options allows for the appropriately sized implant to be selected based on the patient's anatomy. The kit may provide one or more different intervertebral implants, optionally different sized implants, and optionally more than one different sized and/or shaped blades.

In some embodiments the size of the implant is 23 mm×28 mm. In some embodiments, the size of the implant is 26 mm×32 mm. In other embodiments, the size of the implant is 32 mm×38 mm. In some embodiments, the lordosis of the implant is 8°. In other embodiments, the lordosis is 15°. In some embodiments, the implant is 11 mm, 13 mm, 15 mm, 17 mm, 19 mm, or 21 mm high, or any height in between these listed values. An exemplary implant (100) suitable for an anterior approach is illustrated in FIGS. 1A-8B.

The kit may also include toot(s) for placement of the implant and fixation system. In one embodiment, the kit can include tools and materials for inserting bone graft material. For example, the kit can include a syringe or other apparatus for injecting bone graft material.

IV. Methods of Use

A. Preparation of Patient

The intervertebral disc is removed, and the disc space is prepared as usual prior to insertion of the implant. Typically the adjacent inferior and superior endplates are roughened.

B. Implant Sizing and Selection

When selecting an implant, the height, profile, and footprint of the intervertebral space is typically evaluated. One or more trial implants may be inserted into the disc space to find the correct size. Trial implants have the same dimensions as the permanent implants and can be used to visualize the implant positioned in the disc space. Different sized and shaped trial implants are inserted into the disc space until the trial implant with the best contact between both the inferior and superior endplates is found. A mallet or tuning fork can be used to insert and remove the trial implant. Fluoroscopy can be used for visualization.

C. Implant Preparation

Following implant selection, the selected implant is typically loaded with bone graft or bone graft substitute material. For example, as shown in FIG. 1A, bone graft material can be inserted in the opening (160) between the two blades and/or in each or both of the openings (162a and 162b) between the opposite side of each blade and adjacent wall, i.e. a lateral side portion, of the implant. In a preferred embodiment, a volume of bone graft can be loaded into the implant in a range of 2.88 cc to 8 cc, optionally, even greater amounts of bone graft material may be loaded in the implant, such as from about 6 to 20 cc.

In some embodiments, the implant is loaded onto an insertion tool prior to insertion into the spine. While the implant is loaded on the insertion tool, the one or more strike plates are prevented from being deployed due to retention bumps (128a, 128b) located on the exterior retention rail of each strike plate (FIGS. 3, 9A, and 9B), which are in contact with an exterior surface (131) of the implant body (e.g. for an ALIF, this exterior surface is located on the anterior side of the implant body) and protrude slightly beyond the adjacent depression (154a and 154d).

D. Implant Insertion

The implant is inserted into the prepared disc space. If necessary, a mallet can be used to advance the implant into the desired position in the intervertebral disc space. The strike plates are pushed, typically using an insertion tool, until they are fully inside the implant, and in turn, the strike plates deploy the blades, so that the blades are inserted into the inferior and superior vertebral bodies. Preferably, the process of impaction is monitored using fluoroscopy. Finally, a cover plate may be placed over the anterior side of the implant to prevent the strike plates from backing out of the implant. A screw (210) or any alternative fixation device may be placed in the cover plate (200) to secure the plate to the implant. Optionally, the screw is affixed to the cover plate prior to placement of the cover plate on the anterior side of the implant.

E. Optional Reversion

If necessary, following insertion, the implant may be removed from its position in the spine. First, the cover plate (200) is removed by unscrewing the cover plate from the screw hole (152) on the anterior side of the implant. A connection on an inserter is threaded into the threaded holes (140a, 140b) of the one or more strike plates, allowing the one or more strike plates to be pulled out into the insertion position.

The resulting retraction of the blades into the body of the implant allows the practitioner to pull the implant out of, or adjust its position between the adjacent vertebral bodies without destroying the implant.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An implant comprising a body and a bone fixation system,
   wherein the body comprises an interior surface and an exterior surface, the exterior surface including at least a superior surface and an inferior surface disposed opposite the superior surface;
   wherein the interior surface of the body comprises at least two tracks extending in a generally vertical direction oriented between the superior surface and the inferior surface of the body, and
   wherein the bone fixation system comprises at least one blade and at least one strike plate;
   wherein the at least one blade comprises a blade region and a support region,
   wherein the support region of the at least one blade comprises an outer surface, an inner surface, two ends, and an attachment region configured to attach the blade to the strike plate;
   wherein each of the two ends of the blade includes an end protrusion; and
   wherein the end protrusions of the blade fit into the tracks in the interior surface of the body to permit the blade to slide within the tracks and move in the generally vertical direction.

2. The implant of claim 1, wherein the attachment region of the blade comprises a ramp and two side walls.

3. The implant of claim 2, wherein each strike plate comprises a hypotenuse surface that contacts and slides along the ramp in the attachment region of the blade when the strike plate moves.

4. The implant of claim 3, wherein the strike plate further comprises a slot adjacent to the hypotenuse surface and extending generally parallel with the hypotenuse surface.

5. The implant of claim 4, wherein the attachment region of the blade further comprises a pin, wherein each end of the pin attaches to one of the side walls of the attachment region, and wherein the pin is disposed inside the slot of the strike plate and allows the slot to slide along the pin when the strike plate moves.

6. The implant of claim 2, wherein the ramp and side walls define a channel in an attachment region track.

7. The implant of claim 6, wherein the strike plate further comprises a strike plate protrusion comprising the hypotenuse surface, and wherein the strike plate protrusion has a cross sectional shape that is the same as the cross sectional shape of the channel in the attachment region track.

8. The implant of claim 7, wherein the strike plate protrusion has a cross section in a shape selected from the group consisting of dovetails, T-shapes, C-shapes, I-shapes, polygons, rectangles, segments of a circle, and other symmetric or asymmetric shapes.

9. The implant of claim 8, wherein the cross section of the strike plate protrusion is T-shaped, and wherein the cross section of the channel in attachment region track is T-shaped.

10. The implant of claim 1,
    wherein the attachment region of the blade includes a pin;
    wherein the strike plate includes a slot; and
    wherein the blade is attached to the strike plate by the pin.

11. The implant of claim 1, wherein each of the end protrusions has a cross sectional shape selected from the group consisting of dovetails, T-shapes, C-shapes, I-shapes, polygons, rectangles, segments of a circle, and other symmetric or asymmetric shapes.

12. The implant of claim 11, wherein each of the tracks has a cross section in a shape that corresponds with the shape of the cross section of the end protrusions.

13. The implant of claim 1, wherein the end protrusions have cross-sections in the shape of a dovetail, wherein the tracks have cross sections in the shape of a dovetail.

14. The implant of claim 1, wherein the fixation system comprises two strike plates and two blades.

15. The implant of claim 1, wherein the support region of each blade is inside the implant regardless of the position of the strike plate.

16. The implant of claim 1, wherein the implant is a lateral lumbar interbody fusion (lateral LIF) implant.

17. The implant of claim 1, wherein the implant is an anterior lumbar interbody fusion (ALIF) implant.

18. The implant of claim 1, wherein the at least one blade is able to move from a first, insertion position, where the blade region of the blade is disposed inside the implant, to a second, impaction position, where the blade region of the blade protrudes beyond the superior surface or inferior surface of the implant.

19. The implant of claim 1, further comprising a cover plate attached to the exterior surface of the body of the implant, wherein the cover plate retains the at least one strike plate in a position and prevents the at least one strike plate from sliding to a different position.

20. The implant of claim 1, wherein the at least one strike plate further comprises an insertion region configured to mate with a portion of an insertion device to facilitate movement of the strike plate.

21. A kit comprising an implant and a cover plate, the implant comprising a body and a bone fixation system,
  wherein the body comprises an interior surface and an exterior surface, the exterior surface including at least a superior surface and an inferior surface disposed opposite the superior surface;
  wherein the interior surface of the body comprises at least two tracks extending in a generally vertical direction oriented between the superior surface and the inferior surface of the body, and
  wherein the bone fixation system comprises at least one blade and at least one strike plate;
  wherein the at least one blade comprises a blade region and a support region,
  wherein the support region of the at least one blade comprises an outer surface, an inner surface, two ends, and an attachment region configured to attach the blade to the strike plate;
  wherein each of the two ends of the blade includes an end protrusion; and
  wherein the end protrusions of the blade fit into the tracks in the interior surface of the body to permit the blade to slide within the tracks and move in the generally vertical direction.

22. The kit of claim 21, further comprising an insertion tool configured to push the strike plate into an impaction position, wherein in the impaction position the strike plate pushes the blade until the blade region of the blade protrudes beyond the superior surface or inferior surface of the implant.

23. A method of using an implant comprising a body and a bone fixation system,
  wherein the body comprises an interior surface and an exterior surface, the exterior surface including at least a superior surface and an inferior surface disposed opposite the superior surface;
  wherein the interior surface of the body comprises at least two tracks extending in a generally vertical direction oriented between the superior surface and the inferior surface of the body, and
  wherein the bone fixation system comprises at least one blade and at least one strike plate;
  wherein the at least one blade comprises a blade region and a support region,
  wherein the support region of the at least one blade comprises an outer surface, an inner surface, two ends, and an attachment region configured to attach the blade to the strike plate;
  wherein each of the two ends of the blade includes an end protrusion; and
  wherein the end protrusions of the blade fit into the tracks in the interior surface of the body to permit the blade to slide within the tracks and move in the generally vertical direction,
  the method comprising:
    a) inserting the implant into a disc space in the spine of a patient; and
    b) impacting the at least one strike plate, thereby forcing the at least one blade to be deployed superiorly and/or inferiorly so that the blade protrudes beyond the superior surface or inferior surface of the implant.

24. The method of claim 23, wherein during step a), the fixation system is in an insertion position, wherein the at least one strike plate extends beyond one side of the exterior surface of the implant and wherein the blade portion of the at least one blade is disposed inside of the implant.

25. The method of claim 23, wherein prior to step a), the implant is filled internally with bone graft.

26. The method of claim 23, wherein the implant is attached onto an insertion tool prior to step a).

27. The method of claim 23, further comprising attaching a cover plate to the exterior surface on an anterior or lateral side of the implant following step b).

28. The method of claim 23, further comprising, following step b), removal of the implant by pulling the at least one strike plate into the insertion position and retracting the at least one blade inside the implant.

* * * * *